(12) United States Patent
Whitehurst et al.

(10) Patent No.: US 8,888,886 B1
(45) Date of Patent: Nov. 18, 2014

(54) NBPT SOLUTIONS FOR PREPARING UREASE INHIBITED UREA FERTILIZERS PREPARED FROM N-SUBSTITUTED MORPHOLINES

(71) Applicants: Garnett B Whitehurst, New Bern, NC (US); Brooks M Whitehurst, New Bern, NC (US)

(72) Inventors: Garnett B Whitehurst, New Bern, NC (US); Brooks M Whitehurst, New Bern, NC (US)

( * ) Notice: Subject to any disclaimer, the term of this patent is extended or adjusted under 35 U.S.C. 154(b) by 0 days.

(21) Appl. No.: 13/960,196

(22) Filed: Aug. 6, 2013

(51) Int. Cl.
*C05C 9/00* (2006.01)
*C09K 3/00* (2006.01)
*C05G 3/08* (2006.01)

(52) U.S. Cl.
CPC ........................................ *C05G 3/08* (2013.01)
USPC .......................... 71/28; 71/64.07; 252/182.12

(58) Field of Classification Search
USPC .................. 71/28, 29, 30, 64.07; 252/182.12
See application file for complete search history.

(56) References Cited

U.S. PATENT DOCUMENTS

| | | | |
|---|---|---|---|
| 4,517,003 A | 5/1985 | Kolc et al. | |
| 4,530,714 A | 7/1985 | Kolc et al. | |
| 5,024,689 A | 6/1991 | Sutton et al. | |
| 5,352,265 A | 10/1994 | Weston et al. | |
| 5,364,438 A | 11/1994 | Weston et al. | |
| 5,698,003 A | 12/1997 | Omilinsky et al. | |
| 6,030,659 A | 2/2000 | Whitehurst et al. | |
| 6,830,603 B2 | 12/2004 | Whitehurst et al. | |
| 6,852,904 B2 | 2/2005 | Sun et al. | |
| 7,422,680 B2 | 9/2008 | Sheets, Sr. | |
| 7,434,540 B2 | 10/2008 | Aylen et al. | |
| 8,048,189 B2 | 11/2011 | Whitehurst et al. | |
| 8,075,659 B2 | 12/2011 | Wissemeier et al. | |
| 8,133,294 B2 | 3/2012 | Whitehurst et al. | |
| 8,163,058 B2 | 4/2012 | Whitehurst et al. | |
| 8,603,211 B2 | 12/2013 | Rahn et al. | |
| 2004/0163434 A1 | 8/2004 | Quin | |
| 2006/0029567 A1 | 2/2006 | Dutkiewicz | |
| 2006/0185411 A1 | 8/2006 | Hojjati et al. | |
| 2007/0077428 A1 | 4/2007 | Hamed et al. | |
| 2007/0295047 A1 | 12/2007 | Sutton | |
| 2008/0287709 A1 | 11/2008 | Huttenloch et al. | |
| 2013/0145806 A1 | 6/2013 | Iannotta et al. | |
| 2013/0283873 A1* | 10/2013 | Sutton et al. | 71/29 |

FOREIGN PATENT DOCUMENTS

WO   WO/2008/000196   3/2008

OTHER PUBLICATIONS

US 8,425,649, Apr. 2013, Sutton et al. (Withdrawn).

* cited by examiner

*Primary Examiner* — Wayne Langel
(74) *Attorney, Agent, or Firm* — MacCord Mason PLLC

(57) ABSTRACT

Solutions are prepared by dissolving N-(n-butyl)-thiophosphoric triamide (NBPT) in one or more N-substituted morpholines and mixtures thereof. The solutions may be used in urea fertilizers to reduce nitrogen volatilization, or to reduce the odor of animal waste or urine. Methods of preparing urea fertilizers and the resultant products are also described.

37 Claims, 3 Drawing Sheets

Table 1

Density, Freeze Point, Density, and Viscosity for Solution of NBPT in an N-substituted Morpholine (NSM) or mixture of an NSM with an Alkanolamine or an Alkyl Substituted Amino Alcohol Mixture

| Solvent (solvent ratio)[Note 1] | NBPT (%) | pH | Freeze Point (°C) | Density g/mL | Viscosity at 18 °C (cps) | Example |
|---|---|---|---|---|---|---|
| HEM | 24 | 8.65 | <-15 | 1.096 | 95.0 | 5 |
| pH adjusted HEM | 24 | 8.06 | <-15 | 1.103 | 99.4 | 19 |
| pH adjusted HEM | 20 | 8.06 | nd | 1.092 | 94.2 | 1 |
| pH adjusted HEM | 26 | 8.21 | nd | 1.101 | 119 | 2 |
| pH adjusted HEM | 30 | 8.32 | <-15 | 1.103 | 119 | 3 |
| pH adjusted HEM | 36 | 8.40 | <-15 | 1.109 | 154 | 4 |
| pH adjusted HEM and TEA (1:1) | 30 | 8.66 | <-15 | 1.145 | 215 | 6 |
| pH adjusted HEM and Amine G2[Note 2] (1:1) | 24 | 8.56 | <-15 | 1.088 | 164 | 7 |

[Note 1] – the solvent ratio shown is that for the initial mixture before pH adjustment, the final composition is shown in the example text.

[Note 2] – Amine G2 is a mixture of methyldiethanolamine (MDEA) and 2-((2(2-hydroxyethoxy)ethyl)(methyl)amino)ethanol (MHEEA)

Abbreviations: HEM – N-hydroxyethylmorpholine, TEA – triethanolamine, nd – not determined

Figure 1

Table 1

Density, Freeze Point, Density, and Viscosity for Solution of NBPT in an N-substituted Morpholine (NSM) or mixture of an NSM with an Alkanolamine or an Alkyl Substituted Amino Alcohol Mixture

| Solvent (solvent ratio)[Note 1] | NBPT (%) | pH | Freeze Point (°C) | Density g/mL | Viscosity at 18 °C (cps) | Example |
|---|---|---|---|---|---|---|
| HEM | 24 | 8.65 | <-15 | 1.096 | 95.0 | 5 |
| pH adjusted HEM | 24 | 8.06 | <-15 | 1.103 | 99.4 | 19 |
| pH adjusted HEM | 20 | 8.06 | nd | 1.092 | 94.2 | 1 |
| pH adjusted HEM | 26 | 8.21 | nd | 1.101 | 119 | 2 |
| pH adjusted HEM | 30 | 8.32 | <-15 | 1.103 | 119 | 3 |
| pH adjusted HEM | 36 | 8.40 | <-15 | 1.109 | 154 | 4 |
| pH adjusted HEM and TEA (1:1) | 30 | 8.66 | <-15 | 1.145 | 215 | 6 |
| pH adjusted HEM and Amine G2[Note 2] (1:1) | 24 | 8.56 | <-15 | 1.088 | 164 | 7 |

Note 1 – the solvent ratio shown is that for the initial mixture before pH adjustment, the final composition is shown in the example text.

Note 2 – Amine G2 is a mixture of methyldiethanolamine (MDEA) and 2-((2(2-hydroxyethoxy)ethyl)(methyl)amino)ethanol (MHEEA)

Abbreviations: HEM – N-hydroxyethylmorpholine, TEA – triethanolamine, nd – not determined

Figure 2

Table 2

Density, Freeze Point, Density, and Viscosity for Solutions of NBPT in N-substituted Morpholines (NSM's), or mixtures of NSM's, or mixtures of NSM's with an Alkanolamine or an Alkyl Substituted Amino Alcohol Mixture

| Solvent (solvent ratio)[Note 1] | NBPT (%) | pH | Freeze Point (°C) | Density g/mL | Viscosity at 18 °C (cps) | Example |
|---|---|---|---|---|---|---|
| NFM | 24 | 8.41 | nd | 1.155 | 57.3 | 8 |
| pH adjusted NFM | 26 | 8.47 | <-15 | 1.147 | 39.0 | 9 |
| pH adjusted NFM and HEM (1:1) | 24 | 8.24 | <-15 | 1.131 | 59.6 | 10 |
| NAM | 24 | 8.58 | nd | 1.126 | 54.5 | 11 |
| pH adjusted NAM | 26 | 8.43 | <-15 | 1.131 | 163 | 12 |
| pH adjustd NAM and HEM (1:1) | 24 | 8.23 | <-15 | 1.108 | 67.6 | 13 |
| pH adjusted NFM and TEA (1:1) | 24 | 8.72 | <-15 | 1.149 | 215. | 14 |
| pH adjusted NFM and Amine G2 (1:1) | 24 | 8.82 | <-15 | 1.122 | 96.0 | 15 |
| pH adjusted NAM and TEA (1:1) | 24 | 8.50 | <-15 | 1.134 | 313 | 16 |
| pH adjusted NAM and Amine G2 (1:1) | 24 | 8.89 | <-15 | 1.106 | 118 | 17 |
| pH adjusted NFM, HEM and Amine G2 (1:1:1) | 24 | 9.07 | nd | 1.119 | 98.8 | 18 |

Note 1 – the solvent ratio shown is that for the initial mixture before pH adjustment, the final composition is shown in the example text.

Note 2 – Amine G2 is a mixture of methyldiethanolamine (MDEA) and 2-((2(2-hydroxyethoxy)ethyl)(methyl)amino)ethanol (MHEEA)

Abbreviations: HEM – N-hydroxyethylmorpholine, NAM, N-acetylmorpholine, NFM, N-formylmorpholine, TEA – triethanolamine, nd – not determined

Figure 3

Table 3

Volatile Nitrogen Loss for Urea Treated with N-substituted Morpholines (NSM) or mixtures of NSM's with an alkanolamine of an Alkyl Substituted Amino Alcohol

| Solvent (component ratio)[Note 1] | | Percent Volatile Nitrogen Loss (means ± standard error)[Note 2] | | | |
|---|---|---|---|---|---|
| | % NBPT | 3 Day | 7 Day | 14 Day | Example |
| HEM | 24 | 0.137±0.004 | 4.08±0.33 | 13.7±0.8 | 21 |
| pH Adjusted HEM | 24 | 0.139±0.017 | 4.14±0.18 | 12.6±0.9 | 28[Note 3] |
| pH adjusted HEM | 30 | 0.131±0.02 | 3.29±0.22 | 12.7±.06 | 20 |
| pH adjusted HEM + TEA (1:1) | 24 | 0.131±0.015 | 3.17±0.20 | 12.8±0.8 | 22 |
| pH adjusted HEM + Amine G2[Note 4] (1:1) | 24 | ± | ± | ± | |
| NFM | 24 | 0.0652±0.0096 | 1.83±0.29 | 10.9±1.0 | 24 |
| NAM | 24 | 0.0904±0.0111 | 2.18±0.52 | 11.3±0.95 | 25 |
| Control (urea n=7) | 0 | 30.3±1.5 | 35.8±1.2 | 38.1±1.2 | --- |
| Control (urea n=8) | 0 | 23.6±3.0 | 33.2±2.5 | 36.3±2.4 | --- |

Note 1 – the solvent ratio shown is that for the initial mixture before pH adjustment, the final composition is shown in the example text.

Note 2 – n=4 for all samples unless noted otherwise

Note 3 – n = 3

Note 4 – Amine G2 is a mixture of methyldiethanolamine (MDEA) and 2-((2(2-hydroxyethoxy)ethyl)(methyl)amino)ethanol (MHEEA)

Abbreviations: HEM – N-hydroxyethylmorpholine, NAM, N-acetylmorpholine, NFM, N-formylmorpholine, TEA – triethanolamine

NBPT SOLUTIONS FOR PREPARING UREASE INHIBITED UREA FERTILIZERS PREPARED FROM N-SUBSTITUTED MORPHOLINES

BACKGROUND OF THE INVENTION (1) Field of the Invention

The present invention relates to solutions for use in reducing nitrogen volatilization comprising N-(n-butyl)-thiophosphoric triamide (NBPT) dissolved in one or more N-substituted morpholines or mixtures thereof, to methods of making fertilizers using these solutions, and to the resultant fertilizers. The solutions also find utility in reduction of odors from animal wastes.

(2) Description of the Prior Art

Urea is a commonly used nitrogen source in agriculture which is subject to degradation in the soil by action of the enzyme urease. This degradation leads to loss of nitrogen as ammonia in a process known as volatilization. A number of approaches have been tried to protect urea from volatile nitrogen loses including the use of metal inhibitors such as copper salts, or zinc salts, boric acid salts (borates), or sulfur coatings; however; the most effective method is the use of an organic urease inhibitor.

N-(n-butyl)-thiophosphoric triamide (NBPT) is a known urease inhibitor described by (Kolc et. al. U.S. Pat. No. 4,530,714). The compound is a waxy solid with poor water solubility making it difficult to coat urea and achieve adhesion of the compound. The compound undergoes hydrolysis and is thermally unstable. The 714 patent describes the formation of a number of phosphoric or thiophosphoric triamides including N-(diaminothiophosphinyl)morpholine (N-morpholinyl) thiophosphoric triamide), N-(diaminophosphinyl)morpholine.

In the soil, NBPT converts to the phosphoric triamide form (oxon analog) which is the more potent but much more unstable inhibitor (McCarthy, G. W., Bremner, J. M., and Chai, H. S. "Effect of N-(n-butyl)-thiophosphoric triamide on the hydrolysis of urea by plant, microbial and soil urease." Biology and Fertility of Soils Volume 8 Pages 123-127, 1989). For commercial use it is desirable to protect the sulfur atom of the thiophosphoric triamide structure of NBPT until it reaches the soil.

The 714 patent describes the mixing of NBPT with organic solvents (acetone, disobutylketone, methanol, ethanol, 2-propanol, ether (diethyl), toluene, methylene chloride) to distribute the compound into the soil in an effective concentration range which can be anywhere from 5 ppm to 100 ppm depending upon the soil. The organic solvents described by the 714 patent are either too flammable for use or pose significant health risks to be considered suitable for coating urea granules.

In an alternate method, the 714 patent indicates that NBPT can be mixed with solids such as gypsum or clay to distribute the compound into the soil in an effective concentration.

Omilinsky et. al. (U.S. Pat. No. 5,698,003) describes the dissolution of NBPT with a glycol such as propylene glycol or ethylene glycol and esters of glycols. Glycols are compounds with adjacent alcohol groups in the chemical structure. The glycol solvent may contain a co-solvent liquid amide such as N-methyl-2-pyrrolidine and potentially a surfactant or dispersing agent such as polyethylene glycol or esters of polyethylene glycol (polyether alcohols). Other liquid amides disclosed by the teachings of Omilinsky (714 patent) include: formamide, N—N-dimethyl formamide, N,N-dimethyl acetamide, N-butyl N-phenylacetamide. In another group of compounds disclosed as co-solvents by Omilinsky et. al., include intramolecular amides which are heterocyclic structures with a nitrogen atom and oxygen atom on the adjacent carbon such as: N-alkylpyrrolidones. The N-alkylpyyrolidones disclosed in the teaching of Omilinsky et. al. are: N-methyl-2-pyyrolidone (preferred), N-octyl-2-pyrrolidone, and N-dodecyl-2-pyrrolidone. Omilinsky et. al. indicates that esters of glycerol (a triol) may be used as the base solvent. Urea granules containing NBPT are prepared by mixing the urea granules with the NBPT dissolution solvent. Omilinsky et. al. teach that a drying agent such as clay or gypsum may be added to the compositions in the event that a product with excessive wetness is obtained.

Weston et al. (U.S. Pat. No. 5,352,265 and U.S. Pat. No. 5,364,438) teach the dissolution of NBPT in liquid amides such as 2-pyrrolidone or N-alkyl-2-pyrrolidones such as N-methyl-2-pyrrolidone to prepare both solid urea formulations (265 patent) or liquid formulations (438 patent).

Hojjatie et al. (US 2006/0185411) teach the use of a number of sulfur salts of calcium or magnesium (calcium polysulfide, thiosulfate, and magnesium thiosulfate) as urease inhibitors to prepare granular or liquid urea compositions.

Quin (US 2004/0163434) teaches the formation of sulfur coated urea which may contain the urease inhibitor NBPT supplied from a proprietary liquid formulation sold as Agrotain® and distributed by Koch Agronomic Services, Kansas, USA.

Sutton et al. (U.S. Pat. No. 5,247,689) teach the formation of a liquid fertilizer that includes urease inhibitors such as NBPT and nitrification inhibitors such as dicyandiamide in aqueous mixtures of urea ammonium polyphosphate, ammonium thiosulfate and potentially other plant growth improving compounds.

Sutton (US 2007/0295047) teaches the formation of a solid fertilizer comprised of urea and a urea-formaldehyde polymer which may additionally include a urease inhibitor such as NBPT.

Sutton et al. (U.S. Pat. No. 8,425,649) describes a fertilizer additive composed of urea, a urea-formaldehyde polymer and NBPT dissolved in an N-alkyl-2-pyrrolidone.

Hamad et al. (US 2007/0077428) suggests the formation of odor inhibiting fibers (diapers) comprised of a cellulosic fiber and an odor-inhibiting formulation. The odor inhibiting formulation is comprised of an odor inhibiting agent dissolved in hydrophilic or hydrophobic solvent and mixtures of hydrophobic and hydrophilic solvents. The hydrophilic solvents could include amino alcohols such as ethanolamine and diethanolamine. Acids may be added to the odor-inhibiting fiber formulations to neutralize ammonia which may be formed by breakdown of urea. Hamad et. al. (7428 patent) suggests that urease inhibitors such as NBPT may be included in the odor-inhibiting formulation.

Sun et al. (U.S. Pat. No. 6,852,904) suggests the formation of odor controlling cellulosic fibers such as diapers or medical absorbent garments in which a carboxylic acid or partially neutralized carboxylic acid are employed to form the odor-inhibited cellulosic product. The odor-inhibiting formulation may include a transition metal as a hydroxide or oxide which may be used to partially neutralize the carboxylic acid groups.

Dutkiewiez (US 2006/0020029567) teach the formation of odor control formulations using phosphoric triamides including N-(diaminophosphinyl)morpholine, N-(diaminothiophosphinyl)morpholine, N-(diaminophosphinylthiomorpholine), and N-(diaminothiophosphinyl)thiomorpholine for the purpose of odor control. The odor treatments are applied to cellulosic fibers or materials containing animal wastes. Water is used as the NBPT solvent in one example [0261] and methanol in another example [0276] in the teachings of Dutkiewiez.

Cigler (WO 2008/000196) teaches the formation of a solvent system for thiophosphoric triamide solutions comprised of one or more glycol ethers which may optionally contain substances to improve the stability of the thiophosphoric triamde. Examples of stabilizing agents include polyvinylpyyrolidone, N-methylpyrrolidone as crystallization inhibitors. Examples of glycolethers suited to the teachings are diethyleneglycolmonomethylether, dipropyleneglycolether, monomethylether and triethyleneglycolmonomethylether.

Whitehurst et al. (U.S. Pat. No. 8,163,058) teach the formation of fertilizer materials such as granular urea or liquid urea formulations in which the urea is treated with a solution containing NBPT which has been dissolved in an amino alcohol such as diethanolamine, triethanolamine, diisopropanolamine, etc. All carbon chains attached to the nitrogen atom in the solvent system described Whitehurst et. al. contain an alcohol group (058 patent).

Whitehurst et al. (U.S. Pat. No. 8,048,189) teach the formation of a solution of NBPT in a buffered mixture composed of the reaction product of an amino alcohol with a carboxylic acid up to 6 carbons in length.

Whitehurst et al. (U.S. Pat. No. 8,133,294) teaches the formation of various urea containing fertilizers from the buffered mixture of the reaction product of an amino alcohol and a carboxylic acid up to 6 carbons in length. Whitehurst et. al. (U.S. Pat. No. 8,048,189) note that the stability of NBPT is affected by pH when water is present and it is undesirable to formulate a mixture with a pH below 7. All carbon chains attached to the nitrogen atom possess an alcohol group in the amino alcohols used to prepare buffered solvents for NBPT in the teachings of Whitehurst et al. (189 and 294 patents).

Whitehurst et. al. (co-pending U.S. application Ser. No. 13/507,848) describes the use of N-alkyl, N,N-dialkyl amino alcohols and ethers of N-alkyl substituted amino alcohols as solvents for NBPT. These compounds can broadly be described as alkyl substituted amino alcohols (ASAA). The NBPT containing solutions in ASAA can have their pH adjusted with a carboxylic acid. Whitehurst et. al. indicated that the solutions of NBPT in ASAA could have greater protection against crystallization of NBPT at low temperature.

NBPT is synthesized by a reaction process (Kolc et. al 714 patent) that results in the formation of ammonium chloride. This acidic material is often present in commercial NBPT along with ammonia left over from the synthetic process. Huttenboch et. al. (US 2008/0287709) teach the use of apolar amines to remove acids from reaction mixtures including reaction mixtures from the synthesis of NBPT. The apolar amines used to remove acids from NBPT reaction mixtures include N-alkylmorpholines wherein the alkyl group could possess up to 5 carbons; such as N-methyl, N-ethyl, N-propyl, N-butyl, N-pentyl-morpholines. Branched chains of 3, and 4 carbon N-alkylmorpholines are indicated as apolar amines suited to removing acids from NBPT reaction mixtures. Many of these N-alkylmorpholines have low flash points and have strong amine odors potentially limiting their use as solvents for NBPT when preparing granular urea formulations, and could potentially be significant volatile organic carbon emitters in fertilizer formulations.

Urea is a high nitrogen analysis material which is often desirable as a starting material for making additional fertilizer products providing phosphorus or potassium as primary nutrients, calcium, magnesium or sulfur as secondary nutrients or micronutrients such as boron, copper, iron, manganese, molybdenum and zinc.

Whitehurst et al. (U.S. Pat. No. 6,030,659) teaches the formation of phosphate coated urea by first reacting urea with an acid then adding an apatite mineral phosphate source to the surface. Reaction of phosphoric acid while on the urea surface with the apatite mineral is expected to solubilize the apatite mineral to provide available phosphate. It is expected that the acidified coating would help to reduce volatile nitrogen losses from urea.

Whitehurst et al. (U.S. Pat. No. 6,830,603) describes a coating methodology wherein boron containing urease inhibitor compositions may be used to add additional nutrients such as phosphate, potassium, etc. The coating of urea with other materials is known and the references in Whitehurst et al. (603 patent) provides a partial summary of prior art in the area. The inhibitors and binders taught in the 603 patent are aqueous mixtures that include ethanolamine borates, diethanolamine borates or triethanolamine borates and mixtures of these.

Commercial products containing aqueous ethanolamine borates or triethanolamine borates are distributed under the trade name of Arborite® by Encee Chemical Sales, North Carolina, USA. The product is further identified by a binder number for separation of the different mixtures available.

Urea is a common component of animal wastes (manures, green manures, animal bedding materials contaminated with urea, etc.). These animal wastes release ammonia as they decompose due to the action of the enzyme urease. Kolc et. al. (U.S. Pat. No. 4,517,003) disclosed the use of N-acylphosphoric triamides as urease and/or nitrification inhibitors. Kolc et al. (003 patent) include manures in the fertilizers which may be protected from volatile ammonia loss by using a phosphoric triamide. The urease/nitrification inhibitor may be distributed in either liquid form (dissolved in alcohols or halogenated solvents) or in solid form (mixed with clays, vermiculite, gypsum e.g.) to distribute the phosphoric triamide onto a fertilizer (003 patent).

Weissemeier et al. (U.S. Pat. No. 8,075,659) describe the use of urease inhibited fertilizer formulations in which two phosphoric triamide urease inhibitors are used. The phosphoric triamides may be present in the thiophosphoric triamide form. Liquid manures may be treated with the combination of urease inhibitors.

Sheets (U.S. Pat. No. 7,422,680) teach the use of a urease inhibitor such as NBPT in the pretreatment of animal wastes to prevent ammonia release when making fertilizers from animal wastes.

Aylen et al. (U.S. Pat. No. 7,434,540) teach the use of clay based animal bedding material as an absorbent to reduce ammonia levels, odor, microorganisms and insects in animal stalls. The clay based absorbent may contain NBPT as a urease inhibitor.

The use of NBPT or other phosphoric and/or thiophosphoric triamides requires a dispersal mechanism and most of the patents previously identified deal with materials which can be used to disperse NBPT, other thiophosphoric triamides, and phosphoric triamides in liquids or solids. The teachings of the prior art indicate that liquid dispersal agents (solvents) are desired which are safe to handle, easily mix with water, that are stable under somewhat broad temperature conditions and protect the compounds from degradation to unstable forms that are less active as urease inhibitors. A desirable feature for the solvent systems for NBPT is their ability to keep the NBPT dissolved under low temperature conditions. This is made somewhat difficult by the endothermic heat of solution of NBPT and therefore its tendency to crystallize from concentrated solutions at low temperature.

Morpholine is a chemical compound with low molecular weight, which has been used, in many commercial applications. The basic structure of morpholine is that of a six-atom heterocyclic ring composed of an oxygen atom and a nitrogen atom at opposite ends of the heterocyclic ring. The nitrogen and oxygen atom are separated by 2 carbon atoms.

The nitrogen atom of the morpholine structure may be converted into a tertiary nitrogen atom by addition of an alkyl group such as a methyl, ethyl, propyl (isopropyl or n-propyl) or butyl groups (isobutyl, secbutyl, tert-butyl, n-butyl) groups. The alkyl substitutions could potentially contain unsaturated carbon chains. Additionally, the nitrogen atom can be reacted with ethylene oxide, propylene oxide, or butylene oxide to create alkyl structures attached to the nitrogen atom that further possess a hydroxyl group. The nitrogen atom of morpholine can be reacted to form an amide structure such as that of N-formyl morpholine, N-acetyl morpholine, N-propyl morpholine and other 3 or 4 carbon structures in which the N atom of the amide is contributed by morpholine.

SUMMARY OF THE INVENTION

In accordance with the present invention, solutions for use in reducing nitrogen volatilization are prepared by dissolving N-(n-butyl)-thiophosphoric triamide (NBPT) in one or more N-substituted morpholines (NSM) and mixtures thereof. The solutions may optionally contain one or more carboxylic acids having up to 24 carbon atoms to adjust the pH of the solution. The solutions of NBPT in NSM or mixtures of NSM's may be combined with amino alcohols or alkyl substituted amino alcohols (ASAA) and mixtures of alkanolamines and ASAA. The solutions of NBPT in a NSM or mixture of NSM's combined with alkanolamines or ASAA may have their pH adjusted using a carboxylic acid.

The NBPT containing solutions may be applied as a coating for granular urea fertilizers, or mixed with aqueous urea fertilizer solutions. The urea fertilizers may optionally contain other materials such as plant nutrients including micronutrients and denitrification inhibitors. The NBPT containing solutions prepared from N-substituted morpholines or combinations of NSM's with ASAA or alkanolamines may be used to prepare urea fertilizers. A combination of NSM's or a combination of NSM's and alkanolamines or ASAA would be selected to improve adhesion of NBPT to urea, to cause the NBPT solution to penetrate into the granular structure of urea, to control NBPT solution viscosity or to control the crystallization points of the NBPT solutions. The NBPT containing solutions, also, may be used to treat animal wastes containing urea to prevent decomposition of the urea present and denitrification inhibitors may be included in the NBPT solutions when treating animal wastes. Additionally, other urease inhibitors and denitrification inhibitors could be added to the NBPT solutions of the present invention to extend the duration of the urease inhibition or to reduce the loss of urea-N via denitrification reactions.

In general the solvents for N-(n-butyl)thiophosphoric triamide (NBPT) needed to practice the invention are liquids which could be broadly classified as N-substituted morpholines (NSM).

One group of liquid solvents for NBPT can be further described as N-hydroxyalkyl morpholines (NHAM) formula 1:

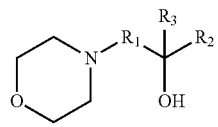

Formula 1 where $R_1$ is a carbon chain from 1 to 4 carbon atoms and $R_2$ and $R_3$ are either hydrogen's or carbon chains with from 1 to 4 carbons. Example compounds include: N-hydroxyethyl-morpholine (HEM) (2-morpholinoethanol), morpholinomethanol, 1-morpholinopropan-2-ol, 1-morpholinobutan-2-ol, 2-methyl-1-morpholinopropan-2-ol, 4-morpholinobutan-2-ol, 3-morpholinopropan-1-ol, and 1-morpholinopropan-1-ol.

Another group of compounds suitable for use as solvents for NBPT can be described a N-amidomorpholines (NAMM) formula 2:

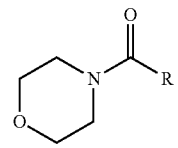

Formula 2 where R is either a hydrogen or a carbon chain with 1 to 4 carbon atoms. All carbon chains could be branched and could be unsaturated carbon chains. It is further understood that R may contain hydroxyl (alcohol) groups. Example compounds include: N-formylmorpholine (NFM), N-acetylmorpholine (NAM), 1-morpholinopropan-1-one, 2-methyl-1-morpholinopropan-1-one, N-morpholinobutan-1-one, N-lactyl (2-hydroxy-1-morpholinopropane-1-one), 2-hydroxy-1-morpholinoethanone, 3-hydroxy-1-morpholinopropan-1-one, 2-hydroxy-1-morpholinopropan-1-one, 4-hydroxy-1-morpholinobutan-1-one, 3-hydroxy-1-morpholinobutan-1-one and 2-hydroxy-1-morpholinobutan-1-one.

The factors which should be considered when selecting the NSM or mixture of NSM's to use as a solvent for NBPT include: solubility limit for NBPT, ability of NBPT solution derived from NSM to withstand low temperature by not forming crystals of NBPT, flammability, and solubility of the resulting solutions in water. NBPT has an endothermic heat of solution and solutions containing the compound may form crystals at low temperature. These crystals of NBPT increase the handling difficulty at low temperature. Materials that can inhibit crystal formation and increase the low temperature usefulness of NBPT solutions are particularly important where nitrogen solutions or granular urea may be used when the ground is still cold and it is necessary to treat urea to protect it from degradation by urease. In addition solutions with low viscosity at temperatures below 0° C. are useful when the coating urea must be performed with cold urea, cold liquids and cold ambient conditions.

Another factor which can be considered, is the ability of the NSM or mixture of NSM's to penetrate the granular urea structure. Some solvent materials containing NBPT will give an oily finish to the urea structure, which can cause sticking in application equipment. Their poor ability to penetrate into the urea structure is particularly noticeable at low temperature. The damp surface with an oily finish can attach to cold application equipment causing the equipment to flow poorly.

Another factor which can be considered when selecting an NSM or mixture of NSM's is the inherent odor of the compound. Some amines are highly volatile and therefore have potentially offensive odors. In addition, these highly volatile materials could be significant sources of potential volatile organic carbon emissions when used to form fertilizer products.

In general NBPT solutions prepared from the NSM or mixtures of NSM's prepared by using N-hydroxyalkylmorpholine (NHAM's) or compounds represented by formulas 1 can have a high pH since these compounds are bases. This can cause ammonia to release from an aqueous solution if ammonia or ammonium salts are present. The high pH will additionally cause ammonia to be released from some granular materials as they are being coated.

In situations where pH control is needed to prevent degradation of a granular or solid material, the pH of the NBPT solution in the NSM may be adjusted with a carboxylic acid thus, producing a mixture of the NSM ammonium ions, NSM, and carboxylate ions of the carboxylic acid. The mixture will additionally contain water, which is generated by the reaction of the carboxylic acid and the NSM. The exact mixture of ammonium ions of the NSM and the NSM will depend upon the molar ratio of the carboxylic acid to the NSM, the ionization constant of the NSM, the pH of the NBPT solution in the NSM provided it is above the $pK_a$ of the carboxylic acid. Should the pH be below the $pK_a$ of the carboxylic acid then the solution will contain mostly the ammonium ion of the NSM, the carboxylate ion, and the carboxylic acid which did not ionize in the reaction with the NSM. The pH adjusted solution of NBPT in an NSM is then used to prepare granular or liquid urea fertilizers, treat manures or treat cellulosic materials.

The acids needed to practice the invention may be described as carboxylic acids with from 2 to about 24 carbons provided that the acid exists as a liquid at room temperature or which may liquefy when heated and held in the heated state at about 40° C. Examples of carboxylic acids which are items of commerce include: acetic, propionic, butyric, valeric, caproic, oleic, linoleic etc. The acids may additionally have an alcohol group such as lactic acid (2-hydroxypropionic acid) which is an item of commerce.

Whenever the NSM belongs to the N-amido morpholines group (NAMM's), the acid will be unable to prevent ammonia release from the solution unless the ammonia is due to residual ammonia remaining from the synthesis reactions of NBPT. In this case the acid will react with the ammonia and form ammonium ions and carboxylate ions of the acid. The exact resulting mixture of ammonia, ammonium ions and carboxylate ions or unreacted acid will depend upon the ammonia content of the NBPT used to form the solution with the NAMM.

Another group of NBPT containing solvent solution can be obtained by the mixing of NSM's with alkanolamines or alkyl substituted amino alcohols (ASAA).

The term alkanolamine will be used to include compounds such as ethanolamine (MEA), diethanolamine (DEA), triethanolamine (TEA), propanolamine, isopropanolamine, dipropanolamine, diisopropanolamine, tripropanolamine, trisopropanolamine and the 4 carbon butanolamine family which includes numerous branched structures.

The term alkyl substituted amino alcohol (abbreviated—ASAA) will be used to refer to compounds which are members of the N-alkyl or N,N-dialkyl amino alcohols or N-alkyl-N-alkoxy amino alcohols. Examples include N-methyldiethanolamine (MDEA), N,N-diethylethanolamine (DEEA), 2-((2(2-hydroxyethoxy)ethyl) (methyl)amino)ethanol (MHEEA).

Another group of NBPT containing solutions can be formed by using a pH adjusted solution of NBPT. This group may be prepared from a mixture of NSM's, ASAA and alkanolamines or mixture of NSM's, alkanolamines and ASAA. The mixture of NSM's, alkanolamines or ASAA can be prepared by mixing NSM's, alkanolamines and ASAA in any order. A carboxylic acid is then added to adjust the pH. The carboxylic acid could contain from 2 to 24 carbons provided that it exists as a liquid at room temperature. These pH adjusted NBPT containing mixtures of NSM's, ASAA and alkanolamines may be used to treat granular urea, aqueous urea solutions, form coated granular urea products with additional nutrients, or treat animal wastes.

The formation of the pH adjusted mixture of an NSM of the N-hydroxalkylmorpholine group (formula 1) with an ASAA or alkanolamines results in the formation of water, carboxylate ions, and ammonium ions of the NSM's, ASAA, or alkanolamines. As indicated above, the composition of the pH adjusted mixture will depend upon: the final pH, the ionization constants (pKa's) of the acid, the ionization constant of each amine containing group present and the molar ratio of carboxylic acid to amine containing functional groups provided by the NSM's, ASAA or alkanolamines.

All of the previously described solutions of NBPT may be used to prepare granular urea fertilizers. These products are preferably prepared from the pH adjusted solutions to reduce the tendency for ammonia release from the urea granule wetted by the solution of the present invention. The NBPT treated granular urea is formed by simply adding the NBPT containing solution to granular urea and mixing to distribute the liquid. Any commercially available mixing equipment can be used to treat the granular urea product with one of the NBPT containing solutions of the invention. The resultant fertilizer product is comprised of urea granules coated with NBPT dispersed in the solvent.

All of the previously described solutions of NBPT may be used to treat aqueous urea solutions. The solutions without pH adjustment could be used when the solution already has ammonia present.

All of the previously described solutions of NBPT may be used to treat animal waste materials. Preferably, the pH adjusted NBPT containing mixtures in NSM's would be used for the purpose of treatment of an animal waste material. The NBPT solution in an NSM solution would be used to reduce the odor of the animal waste material.

All of the previously described solutions of NBPT dissolved in NSM's can be used to prepare aqueous urea solutions which contain additional nutrients and NBPT. The additional nutrients can be added as liquids or solids.

All of the previously described solutions of NBPT in NSM's can be used to form granular urea products with additional nutrients that contain NBPT. The additional nutrients are typically added to the surface of the granular urea in powdered form. The powders can be produced by any dry grinding process. The production of granular urea with additional nutrients containing NBPT may require the use of additional liquid acting as a binding agent or as a liquid which can serve as both a diluent for the NBPT containing solution and binding agent. The resultant fertilizer is comprised of urea granules, with a first coating of NBPT dispersed in the selected solvent, components of an optional diluent for the NBPT solvent or components of an additional liquid binding agent, and an outer coating of the additional nutrients. The outer coating could be applied in several layers.

The amount of urease inhibitor NBPT needed in a given urea fertilizer product produced according to the invention often depends upon the soil type and soil pH and the amount of urease activity due to soil bacteria. The quantity of urease inhibitor needed in the final liquid or granular product treated with an NBPT containing solution could be determined by measuring the urease activity in a range of soils and then determining the amount of inhibitor needed to inhibit that amount of urease in the specific soil where the urea containing products will be applied. The alternative method involves assessing the volatile nitrogen losses from a range of soils and formulating with the needed NBPT containing solution to achieve control of the volatile nitrogen loss in the specific soil where the liquid or granular treated products will be applied Generally the effective amount of NBPT which will need to be added to treat urea fertilizers will lie within the range of 0.005% to 0.25% depending upon the product and the conditions where the NBPT containing product will be applied. When treating an animal waste, dilution of a concentrated NBPT solution with an aqueous solution may be required to achieve an effective dose within the range of 0.005% to 0.25%.

As used herein, the term "urea fertilizer" encompasses urea and mixtures of urea with other primary nutrients, secondary nutrients and/or micronutrients. Preferably, urea comprises at least 10% by weight of the urea fertilizer (dry weight basis). Unless otherwise noted all percentages refer to weight percentages or parts per 100 parts.

As used herein the term animal waste is understood to include manures, green manures, animal bedding materials or other products which could contain urea derived from the liquid and/or solid excrement of any animal. These animal waste products are sometimes called reduced nitrogen fertilizers.

The term solubility limit as used below refers to the measurement of maximum amount of NBPT which will dissolve in an NSM, mixture of NSM's, or mixture of an NSM or NSM's with alkanolamines or ASAA. The term solubility limit would also apply to the pH adjusted solutions of NBPT dissolved in an NSM, mixtures of NSM's, or mixtures of an MSM or NSM's with alkanolamines or ASAA. The NBPT containing solution is observed over a period of time to assess whether solids form upon standing. If solids form upon standing the solution is deemed unstable and the solubility limit is considered exceeded. All solubility limits are expressed in weight percentages and are understood to imply the limit of the solubility of NBPT.

Additionally, the practice of the invention may include other items of commerce including ethylene glycol and propylene glycol. The glycols can be used as co-solvents to control spreadability of a formulation. Additionally, other materials such as glycol ethers and/or nonionic surfactants may be included in the formulation to improve sprayability and/or surface coating behavior. The glycol ethers and/or nonionic surfactants quite often work by lowering the surface tension of aqueous solutions to permit the liquid to more effectively wet a surface. The glycol ethers may increase the adhesion of the liquid coating to the fertilizer substrate.

Additionally, a colorant or mixture of colorants may be used to help the user determine when the urea containing material has been treated. In some cases it may be necessary to add some alcohol, glycol, glycolether such as diethylene glycol, a polymeric glycol, or polymeric glycol ether to the solution of the present invention containing NBPT to help disperse the colorant or mixture of colorants.

The production of some coated granular products may include one or more sources of additional plant nutrients as water soluble salts such as ammonium sulfate, monoammonium phosphate, potassium chloride, potassium dihydrogen phosphate, potassium sulfate, and salts of iron, copper, zinc, manganese, and others; and partially water soluble salts such as gypsum, potassium magnesium sulfate and others commonly employed in agricultural practice. The only requirement for the selection of the additional plant nutrient source is that of compatibility with urea. Compatibility of many fertilizer materials can be determined from the "Farm Chemicals Handbook" published by Meister Publishing Co. Ohio, USA.

To make coated granular urea fertilizers containing additional nutrients using the NBPT containing solution of the invention, one or more materials providing plant nutrients other than urea is preferably used in a powdered form. The term powder for purposes of the invention shall mean any finely divided substance prepared by some dry grinding process. There are numerous forms of dry grinding equipment available including hammer mills or pin mills, etc. A powder for purposes of the invention shall imply any finely divided material with a particle size less than 0.300 mm (300 μm).

When preparing the coated granular urea fertilizers with powdered nutrients, the NBPT containing solution will generally need to be diluted to concentrations below about 5% to avoid using too much NBPT in the product. The dilution may be made in a number of aqueous liquids, liquids such an aqueous ethanolamine borate, diethanolamine borate, triethanolamine borate sold under the trade name of Arborite®. The diluent liquid could be an available aqueous liquid fertilizer solution. Alternatively, the NBPT containing solutions of the present invention may be prepared at a lower concentration to prepare the powder coated product. An NBPT containing solution of the present invention may be mixed with another liquid such as aqueous urea solution to provide the liquid required to cause adhesion of the powder(s) to granular urea. To enhance the properties of the diluent liquid, denitrification inhibitors may be added to the diluent solution to produce coated urea products with additional nutrients which are protected from both volatile nitrogen losses and nitrification losses.

To form the powder coated granular urea product, the granular urea may be treated with the NBPT containing solution and other binding agents or nitrification enhanced diluent to form a surface wetted urea product and then the powdered nutrients are added to complete the coated NBPT containing granular product. In an alternate method suited to continuous processing, the powder may be mixed with the granular urea and then an NBPT containing solution of the present invention or a diluted NBPT formulation of the present invention added while continuing to mix the combined mass until the powder has adhered to the urea. In a another alternative method of forming the powder coated urea product containing NBPT, granular urea previously treated with the NBPT containing solutions of the present invention may be used and then another binding agent employed to cause the powders to adhere to the urea employed. The method of preforming an NBPT treated urea, then forming the powder coating on top of the NBPT treated urea has the advantage of allowing the production process to be separated from the powder coating process in time or allowing the powder coating to be performed using separate equipment. As an added advantage the separation of the NBPT treatment from the process of producing the powder coated urea method allows time for the NBPT treatment to interact with the urea granule such that the NBPT can penetrate and fill pores within the granular structure. Any commercially available mixing equipment may be employed to prepare the powder coated urea product containing NBPT and additional plant nutrients.

Fertilizer compositions are described by expressing the weight percentage of the primary elements present in the following manner: XX-YY-ZZ; where XX is the percentage of nitrogen, YY is the phosphate percentage expressed as $P_2O_5$, and ZZ is the potassium content expressed as the percentage $K_2O$. When secondary elements are present the percentages are often listed after the primary elements in the order calcium, magnesium and sulfur or by stating the analysis for the secondary element followed by the symbol for the element. For example a 35-9-0-2% Ca-2Mg,-3S would indicate a material (fertilizer) with 35% nitrogen, 9% $P_2O_5$, 0% $K_2O$, 2% Ca, 2% Mg and 3% S.

When adding any of the NBPT containing solutions described above to aqueous liquid urea fertilizer solutions, additional soluble salts which could be pre-dissolved into an aqueous solution may be added to the solutions to provide other nutrients required for growth of the plant species. Ammonium thiosulfate, ammonium sulfate, potassium chloride, potassium sulfate, manganese (II) sulfate, magnesium sulfate, ammonium phosphate, ammonium polyphosphate, water soluble salts of copper and zinc, ammonium molybdate, sodium molybdate, borates (ammonium, potassium and sodium salts of boric acid) are examples of materials which may be used to provide additional nutrients depending upon the growth requirements of the plant species. In addition to the soluble salts other materials which promote growth such as plant hormones or hormone analogs could be added, chelating agents such as EDTA (ethylene diamine tetraacetic acid), citric acid, gluconic acid, glucoheptonic acid in either the acid form or salt form to prevent metal ion precipitation from the aqueous solution as insoluble hydroxides or carbonates; and materials which cause the liquid to disperse more uniformly across plant leaves such as wetting agents or "spreader stickers" as they are sometimes called in the agricultural industry might be added. Ligninsulfonates which are derived as a byproduct of wood pulping operations are sometimes used in agriculture as both metal sequestering agents and wetting agents could be used. These additional nutrients, growth regulators, chelating agents, sequestering agents or wetting agents could be added singly or in combination.

Denitrification inhibitors are other products which could be added when forming liquid or granular urea products of the present invention, or treating manures (animal wastes) with one of the solutions of the present invention. Examples of denitrification inhibitors include: dicyandiamide (DCD or 2-cyanoguanidine), DMPP (3,4-dimethylpyrazole phosphate), nitrapyrin (2-chloro-6-(trichloromethyl)pyridine). Nitrapyrin is sold as the product N-Serve® by Dow Chemical Company, Michigan USA. To form a liquid product which contains the denitrification inhibitor, the denitrification inhibitor could be added along with one of the NBPT containing solutions of the present invention when preparing the urease inhibited and nitrification protected liquid fertilizer composition. The NBPT solution of the present invention and the denitrification inhibitor could be added as separate ingredients to the solution prepared for field application. If the denitrification inhibitor is soluble in an NBPT containing solution of the present invention, then a product containing both ingredients could be made to supply the urease inhibitor and denitrification inhibitor to prepare urea liquid or granular fertilizers. To make a urease inhibited denitrification inhibited coated granular urea product with other nutrients, the denitrification inhibitor could be added via an aqueous solution used to dilute one of the NBPT containing solutions of the present invention when preparing the coated granular urea product containing additional nutrients. The denitrification inhibitor could be added in a separate coating step.

Other ingredients which could be included in the NBPT containing formulations of the present invention include: odor masking agents such as pine oils, perfumes, etc. Odor masking agents would be useful when treating animal bedding materials and manures. Additionally, a second urease inhibitor could be included such as phenylphosphoric diamidate or phenylthiophosphoric diamidate, N-(diaminophosphinyl)morpholine, N-(diaminothiophosphinyl)morpholine, N-(diaminophosphinylthiomorpholine), and N-(diaminothiophosphinyl)thiomorpholine.

BRIEF DESCRIPTION OF THE DRAWINGS

FIG. 1 is Table 1.
FIG. 2 is Table 2.
FIG. 3 is Table 3.

DETAILED DESCRIPTION OF THE INVENTION

NBPT—N-(n-butylthiophosphoric triamide) is an item of commerce.

Urea ammonium nitrate solutions (UAN) are items of commerce which may contain from 26% N (total) to 32% N (total).

Granular urea is an item of commerce with a fertilizer analysis of 46-0-0. The product may be obtained as granules ranging in size from 1 mm to 10 mm.

The term: N-substituted morpholine (NSM) will be used to describe compounds which contain a carbon chain attached to the nitrogen atom of the morpholine structure and could further be classified as: N-hydroxyalkylmorpholines (compounds defined by formula 1 above), N-amidomorpholilnes (compounds defined by formula 2 above) or N-alkylmorpholines (compounds defined by formula 3 above). It is understood that the term NSM may refer to a mixture of N-hydroxyalkylmorpholines, N-amidomorpholilnes, and N-alkylmorpholines.

N-methylmorpholine (NMM), N-ethylmorpholine (NEM), N-hydroxyethylmorpholine (HEM), N-formylmorpholine (NFM), and N-acetylmorpholine (NAM) are items of commerce which may be used to practice the invention.

The term: alkyl substituted amino alcohol (ASAA) will be used to refer to compounds that could be further classified as N-alkyl or N,N-dialkyl amino alcohols or compounds that could be further classified as N-alkyl-N-alkoxy amino alcohols. It is further understood that the term ASAA may imply a mixture of N-alkyl, N,N-dialkyl, and/or N-alkyl-N-alkoxy amino alcohols.

N-methylethanolamine (NMEA); N-methyldiethanolamine (MDEA), N,N-dimethylethanolamine (DMEA) and N,N-diethylethanolamine (DEEA) are items of commerce which can be used in the practice of the invention. Additionally, mixtures of N-alkyl amino acohols and N-alkyl-N-alkoxy amino alcohols are particularly useful as solvents for NBPT. One such example is a mixture of N-methyldiethanolamine (MDEA) and 2-((2(2-hydroxyethoxy)ethyl) (methyl)amino)ethanol (MHEEA) which is commercially available as the product Amine G2 from Dow Chemical Company, Michigan, USA. The percentages of MDEA and MHEEA present in the mixture actually used will be provided in parenthesis e.g. Amine G2 (24% MDEA, 74% MHEEA).

The term alkanolamine will be used to refer to compounds which generally could be described as possessing a nitrogen atom which is connected to one or more carbon chains which all possess an alcohol functional group. These compounds are generally the reaction products obtained when oxiranes are reacted with ammonia. The following alkanolamines are items of commerce which could be used in the practice the invention: ethanolamine (MEA), diethanolamine (DEA), triethanolamine (TEA), propanolamine, isopropanolamine (IPA), diisopropanolamine (DIPA).

The term carboxylic acid shall imply a chemical structure containing one or more carboxyl groups. The carbon chain may be from 2-24 carbons in length provided that the material is a liquid. Acetic acid, propionic acid, lactic acid, oleic acid are liquid carboxylic acids which are commercially available and could be used to practice the invention.

To assist in the formulation processes described below, a dye or colorant can be added. Any commonly used colorant may be added to the mixture to provide visual evidence of the uniformity of the distribution of the NBPT containing solutions described below. Depending upon the dye or colorant chosen an alcohol such as methanol, ethanol, propanol, 2-propanol, or butanol e.g. may be required to help disperse the colorant into the NBPT containing solutions described below.

The following colorants are items of commerce: Orcobrite® 4BN pigment violet (concentrate) sold by Organic Dyestuffs Rhode Island, USA, Intrabond® Liquid Violet 5BF (concentrate), or FDC Yellow Number 6 sold by Sensient Technologies Corporation Wisconsin, USA.

To practice the invention, a solution of NBPT is prepared by melting NBPT into a liquid NSM or a mixture of NSM's by heating the liquid mixture containing NBPT to a temperature sufficient to cause the NBPT to melt into the mixture and holding the temperature until all of the NBPT is dissolved. Generally a temperature between 30° C. and 50° C. is adequate to form the initial NBPT solution in the NSM and preferably a temperature from 40° C. to 45° C. will be used to dissolve the NBPT in the NSM. Heating may be accomplished by any commonly used heating mechanism such as a jacketed vessel or a heat exchanger system. The initially formed NBPT containing solution in the NSM may then be modified by adjusting the pH as described below or may be used without pH adjustment to add NBPT to: aqueous urea solutions, granular urea products or animal wastes as described below.

The NBPT concentration of the NBPT solution in the NSM or mixture of NSM's will typically lie within the range of 0.5% NBPT to 40% NBPT. The upper limit is determined by the solubility limit of NBPT in the NSM or mixture of NSM's over the temperature range of use. The lower limit for the NBPT concentration is determined by the application where the solution will be used and will usually be below the solubility limit.

When pH control is required for the NBPT solution in an NSM or mixture of NSM's, the pH of the initial solution of NBPT in an NSM or mixture of NSM's may be adjusted by reaction of the NBPT containing solution in an NSM or mixture of NSM's with a liquid carboxylic acid containing from 2 to 24 carbons. The reaction of the NSM or mixture of NSM's and a carboxylic acid is exothermic and may require cooling. The pH of the carboxylic acid containing mixture should be from 7 to 10, but preferably from 8 to 9. The reaction of an NSM with a carboxylic acid forms water, the ammonium ion form of the NSM, and the carboxylate ion of the carboxylic acid. When the solution is formed with a mixture of NSM's then a mixture of ammonium ions of the NSM's will be present.

Depending upon the $pK_a$ of the NSM or compounds within the mixtures of NSM's, the $pK_a$ of the carboxylic acid, and the molar ratio of the NSM or mixture of NSM to the carboxylic acid, the pH adjusted mixture resulting from the reaction will contain the NSM, the respective ammonium ions of the NSM or a mixture ammonium ions of the NSM's, the NSM or mixture of NSM's, a carboxylate ion and water. The water will be present in an amount equal to the moles of carboxylic acid that reacted with the NSM or mixture of NSM's. If the final pH is below the $pK_a$ of the carboxylic acid and the $pK_a$ of the NSM present the pH adjusted mixture will contain a carboxylic acid, carboxylate ion, the ammonium ion of the NSM (or NSM's) and water. Generally, it is preferred that the solution pH be above that of the $pK_a$ of the carboxylic acid to prevent degradation of NBPT in the acidic solution.

The NBPT concentration in the pH adjusted NBPT solution in an NSM (or mixture of NSM's) will typically lie within the range of 0.5% NBPT to 40% NBPT. The upper limit is determined by the solubility limit of NBPT in the pH adjusted NSM solution or the solubility limit of NBPT in the mixture of NSM over the temperature range of use. The lower limit for the NBPT concentration is determined by the application where the solution will be used and will usually be below the solubility limit.

Generally, the pH adjusted solution of NBPT in an NSM (or mixture of NSM's) is required whenever an alkaline solution containing NBPT in an NSM could cause ammonia to release from an aqueous solution or a solid substrate. Granular urea can contain traces of ammonium carbamate, which when contacted by an alkaline material will form ammonia vapor. Some aqueous urea solutions such as urea ammonium nitrate (UAN) typically have an ammonia odor, thus, the pH adjusted NBPT containing solution does not need to be used.

The pH adjusted NBPT solution in a NSM would be more suited to treatment of manures that typically release ammonia as the urea (from urine) degrades due to bacterial action.

In another embodiment of the invention, an NSM or mixtures of NSM's may be combined with alkanolamines, ASAA, or mixture of alkanolamines and ASAA to prevent NBPT crystallization from solutions prepared from alkanolamines, ASAA, or mixtures of alkanolamines with ASAA when carboxylic acids have been added. Solutions of alkanolamines or ASAA can be very unstable when carboxylic acids are present. The crystallization inhibited pH adjusted solutions of NBPT in the mixture of NSM with alkanolamines, ASAA or mixture of alkanolamines and ASAA are formed in the same manner as described above for NSM.

The NBPT concentration of the pH adjusted NBPT crystallization inhibited solution in a mixture of NSM with alkanolamines, ASAA, or mixture of alkanolamines and ASAA will typically lie within the range of 0.5% NBPT to 40% NBPT. The upper limit is determined by the solubility limit of NBPT in the mixture of NSM with the alkanolamine, ASAA or mixture of alkanolamine or ASAA over the temperature range of use. The lower limit for the NBPT concentration is determined by the application where the solution will be used and will usually be below the solubility limit.

In the preferred embodiment of the invention for treatment of an aqueous urea solution such as urea ammonium nitrate (UAN solution); the solution of NBPT formed as described above in an NSM or mixture of NSM's is added to UAN solution to provide an NBPT concentration from 0.005% NBPT to 0.25% NBPT. The amount actually added will depend upon the formulation and would generally reflect the amount of urea within the aqueous urea formulation Alternatively, the addition of NBPT to an aqueous urea solution such as UAN may be accomplished using a pH adjusted solution of NBPT prepared in an NSM and or mixture of NSM's. Alternatively, the addition of NBPT to an aqueous urea solution such as UAN may be accomplished using a mixture of NSM, alkanolamines, or ASAA. Alternatively, a pH adjusted mixture of NSM, alkanolamines, or ASAA may be used to treat an aqueous urea solution such as UAN.

When treating an aqueous urea solution with the NBPT containing solutions of the present invention, the NBPT containing solution may be added to a fertilizer tank mix prior to application to the field crop. The term tank mix as used above refers to a solution prepared for application to a field crop. Such solutions are well known in the agricultural industry. The solution could be prepared in bulk at a solution fertilizer distributor for use by the fertilizer applicator.

Fertilizer tank mixes may contain other materials such as additional nutrients, growth promoting compounds such as plant hormones, chelating's agents, wetting agents, and the NBPT dissolved in one of the solutions of the present invention. The mixing order is not critical unless metal salts prone to hydroxide or carbonate formation are included in the tank mix (copper, iron, manganese, zinc e.g.). Whenever a metal salt prone to hydroxide or carbonate formation is included in the tank mix then a chelating agent should be dissolved into the tank mix before adding the metal salt prone to hydroxide or carbonate formation. Examples of chelating agents include: EDTA, HEDTA, citric acid, gluconic acid, glucoheptonic acid and their ammonium, potassium, or sodium salts. Mixtures of chelating agents could be used.

Commercially available chelated metal micronutrient solutions could be used to supply the water soluble metal ions for the tank mix solution containing urea, NBPT and other nutrients.

UAN solutions are sometimes mixed with ammonium thiosulfate solutions to provide both nitrogen and sulfur to plants. In an embodiment of the invention, this N and sulfur supplying UAN—ammonium thiosulfate solution can be treated to protect the urea from urease hydrolysis by adding one of the NBPT solutions of the present invention to the mixture of UAN solution and ammonium thiosulfate solution.

In the preferred embodiment of the invention to form NBPT treated granular urea fertilizers, the pH adjusted NBPT solution in an NSM or mixture of NSM's would be used. For the treatment of a granular urea fertilizer the concentration of NBPT in the NSM solution or mixture of NSM's would range from about 0.5% NBPT to about 40% NBPT. After dissolving the NBPT in the NSM or mixtures of NSM the carboxylic acid component is added and the pH is adjusted to between 8 and 9. Granular urea is then treated with the solution of NBPT dissolved in the pH adjusted solution of NSM or mixture of NSM's to achieve an NBPT concentration in the treated urea from 0.005% to 0.25% by weight NBPT. The treatment of the granular urea substrate may be performed in any convenient mixing equipment commonly employed in the fertilizer industry for similar purposes.

The coating of granular urea with NBPT dissolved in a pH adjusted solution of the present invention may be accomplished using any commercially available equipment in which a granular product may be comingled with a liquid. The general procedure is to charge the mixing equipment with granular urea and then add the required amount of the pH adjusted NBPT containing solution of the present invention needed to provide the NBPT for the final product. The combined mass is mixed to distribute the liquid onto the surface of the granular urea particle. The equipment may permit the pH adjusted solution of NBPT to be sprayed onto the granules as they tumble in the mixer or the pH adjusted solution of NBPT may be added into the granules as they tumble within the mixing equipment. The surface wetted granules from addition of the pH adjusted solution containing NBPT are then tumbled until the material has been uniformly distributed across the surface of the granules. The resulting NBPT treated urea product may then be stored or packaged as required. A flow ability aid or desiccant such as gypsum, diatomaceous earth, silica, monoammonium phosphate, potassium sulfate, potassium magnesium sulfate or clay may be required to ensure flow ability of the resulting coated granular product if there is inadequate control of the volume of the pH adjusted NBPT solution. Preferably, the pH adjusted solution containing NBPT is introduced into the mixing equipment via a metering system able to provide reproducible formulations.

The NBPT coated urea product produced with the pH adjusted NBPT containing solution of the present invention may be applied to soil to provide nitrogen needed by plants which contain the valuable urease inhibitor NBPT. The granular product materials containing NBPT may be applied using any routinely used application method such as broadcast by ground or aerial spreading equipment, banding using ground application equipment and spotting techniques wherein the fertilizer is placed next to the plant either above ground or in a depression made into the soil surface next to the plant.

In an alternate embodiment of the invention, the NBPT coated granular urea fertilizer products can be obtained by using a solution of NBPT in a NSM or mixture of NSM's with an alkanolamine, ASAA, or mixture of alkanolamines and ASAA. The solution would not be formed by addition of a carboxylic acid. The process of forming the NBPT coated granular urea product is the same as described above for the pH adjusted NBPT solutions in NSM or mixtures of NSM's.

In another embodiment of the invention the treatment of granular urea with NBPT could be performed using a pH adjusted NBPT containing solution prepared by mixing an NSM (or mixture of NSM) with an alkanolamine or ASAA. The process of forming the NBPT coated granular urea product is the same as described above for the pH adjusted NBPT solutions in ASAA or mixtures of ASAA.

Other useful granular urea products may be prepared by using the NBPT containing solutions of the present invention as part of the binding agents needed to cause powdered materials to adhere to granular urea. In general there is a liquid to powder ratio which must be determined to cause a powder to adhere to granular urea surface. This liquid to powder ratio depends upon the nature of the powder and will vary with different materials. Generally, the amount of liquid required to form the NBPT coated granular urea products containing additional nutrients is greater than that needed to form a granular urea containing NBPT without additional nutrients; therefore, the NBPT containing solution of the present invention will need to be diluted to avoid potential phytotoxic concentrations of NBPT in the powder coated granular urea product.

In one embodiment of the invention to prepare the NBPT containing granular urea with additional nutrients, the NBPT concentration of the NBPT containing solutions of the present invention may need to be prepared at a lower concentration. Generally, the concentration of NBPT in a solution of the present invention need to be less than about 5% when preparing NBPT containing granular urea products with additional nutrients.

In another embodiment of the invention the NBPT containing solution in of the present invention may be diluted. The dilution of a NBPT containing solution of the present invention is accomplished by adding other liquids including aqueous mixtures. The resulting diluted NBPT containing mixture derived from the solutions of the present invention can then be used to cause powdered plant nutrient supplying materials to adhere to granular urea.

In another embodiment of the invention, the NBPT concentration of the solutions of the present invention may be reduced at the time the coated products are produced by adding the NBPT containing solution of the present invention along with another solution to the granular urea before adding the powders. This technique is very convenient for batch mixing operations and lab scale production. Any of the diluent solutions described below may be used to provide the additional liquid needed for adhesion of the nutrient powder to the urea.

Examples of solutions which may serve as diluents and binding agents for any of the NBPT containing solutions of the present invention include: UAN solutions, UAN solutions blended with aqueous ammonium thiosulfate solution, aqueous ammonium sulfate solutions, aqueous solutions containing phosphates such as potassium phosphate solutions, ammonium phosphate solutions, ammonium polyphosphate solutions, aqueous solutions of metal nitrates such as nitrates of calcium, copper, iron, magnesium, manganese, potassium, and zinc or mixtures of metal nitrates, or aqueous solutions of metal acetates. Mixtures of the aqueous solutions indicated could be used provided that the materials are chemically compatible with one another. Other examples of solutions which could be used are the binding agents such as Arborite® Binder 77 (aqueous triethanolamine borate) Arborite® Binder 75 (aqueous copper ethanolamine complex and copper (II) borate mixture) both of which are sold by Encee Chemical Sales North Carolina, USA. Aqueous carboxylic acid salt solutions not containing NBPT prepared by reacting an ASAA or mixtures of ASAA with or without or alkanolamines and a carboxylic acid may be used as a diluent or binding agent. One example of an aqueous amino alcohol salt solution is an aqueous solution of triethanolamine acetate which may be prepared by reacting acetic acid and triethanolamine. Another example of a binding solution which is an aqueous carboxylic acid salt solution is a solution which contains a mixture of the reaction products of acetic and oleic acid with triethanolamine.

Coated granular urea products containing additional plant nutrients are then prepared from granular urea, a source or sources of the additional nutrients in powdered form and the diluted NBPT containing solution of the present invention described above. Granular urea is first dampened with the diluted NBPT containing solution of the present invention and the materials are mixed to distribute the NBPT containing liquid mixture over the granular urea surface. Any commonly used equipment to comingle a liquid with a granular solid may be used to accomplish the coating process. After distribution of the diluted NBPT containing solution over the granular surface, the additional nutrients in powdered form are added to the dampened mixture and the resulting combined ingredients are further mixed to distribute the powdered materials.

In an alternate embodiment of the invention for forming the powder coated NBPT containing urea fertilizer, an NBPT containing solution of the present invention and a diluent liquid or binding agent are added to the granular urea first, the ingredients are then tumbled, and finally the powdered nutrient source is added and the mixing is continued to distribute the powder throughout the NBPT containing and liquid wetted urea.

In an another alternate embodiment for forming the powder coated NBPT containing urea, powdered materials may be first mixed with the granular urea and then the NBPT containing diluted mixture is sprayed onto a tumbling bed of the dry ingredients to agglomerate the dry materials. This later method is particularly suited to continuous processing.

In an another alternate embodiment for forming the nutrient powder coated NBPT containing coated urea may be prepared from NBPT containing solution of the present invention may be formed without pH adjustment. The process of forming the NBPT coated urea fertilizers with powdered nutrients is the same as that described for using the pH adjusted NBPT solutions of the present invention.

As another embodiment of the present invention to form a nutrient supplying powder coated urea containing NBPT, the granular urea is first treated with the NBPT containing solution and that NBPT coated urea product may be stored until used to form the nutrient powder coated granular urea product. The pre-treatment of the granular urea with the NBPT containing solution has advantages when it is more convenient to separate the NBPT treatment from the nutrient powder coating process, and when it may be desirable to add other external coatings on top of the nutrient powder coating. The central NBPT treated urea granule, thus, is protected from the operations needed to add the additional layers of material to the granular product.

Occasionally, a nutrient powder coated granular urea containing NBPT produced in accordance with the description above may form a pile set when stored. The pile set can be prevented during manufacture or broken after manufacture by adding a metal stearate. Calcium, magnesium and zinc stearates are items of commerce which can be used to disrupt surface adhesions which form in the nutrient powder coated urea containing NBPT. Clays and gypsum will work for the purpose of disrupting the pile set. The pile set disrupting ingredient is typically added after the nutrient powder coated urea with NBPT granule is formed. The pile set disrupting ingredient is typically added in amount which represents less than about 1% of the formulation.

Finally, any of the granular urea products produced as described above may be treated with a de-dusting agent to protect the product from shipping damage. The de-dusting agent may be added at the point of manufacture or the point of shipping. De-dusting agents are common in the fertilizer industry and heavy oils are often used in the fertilizer industry for de-dusting purposes.

As other embodiments of the present invention, animal wastes (manures) may be treated with any of the NBPT containing solutions of the present invention. Preferably pH adjusted solutions would be used. The NBPT solution of the present invention could be sprayed onto the manure before collecting for field application or added to the tank used for field distribution or storage. Once added to the tank it would be necessary to mix the materials to distribute the NBPT throughout the manure. Hays and other bedding materials are often placed in animal stalls and alternatively, the bedding materials could be treated with one of the NBPT containing solutions of the present invention, to decrease the rate of hydrolysis of urea present in the animal urine and reduce ammonia odors. An odor masking compound could be added to the NBPT solution in an ASAA (or mixture) to mask odors from other compounds in the animal wastes.

The NBPT treated manures could be further treated for ecological protection of ground waters by adding a denitrification inhibitor to prevent the conversion of nitrogen materials in the manures to nitrates and subsequently to NO or $N_2O$, which escape to the atmosphere. These denitrification processes result in the loss of the fertilizer nitrogen value of the applied manure.

Additional volatility control could be achieved if needed by using a second urease inhibitor such as phenylphosphoric diamidate, N-(diaminophosphinyl)morpholine, N-(diaminothiophosphinyl)morpholine, N-(diaminophosphinylthiomorpholine), or N-(diaminothiophosphinyl)thiomorpholine.

The following examples are provided to represent the practice of the invention. Other embodiments could be recognized by anyone skilled in the art by reading of the previous description and examples described below and are properly within the scope of the present invention.

EXAMPLES

The term powdered when used is understood to refer to any finely divided material with a particle size less than 250 μm (−60 mesh).

In many of the following examples the term melted is used to describe the process of dissolving NBPT into a solvent system. The term melted within this context refers to the heating of the mixture of NBPT and a solvent or mixture of solvent materials to dissolve the NBPT. The dissolution step requires a temperature of between 30° C. and 50° C.

In some of the examples which follow an amine functional group is reacted with a carboxylic acid. The reaction generates an ammonium ion from the amine and a carboxylate ion from the carboxylic acid employed. The reaction, also, generates water in an amount equivalent to the amount of the carboxylic acid which reacted. The quantity of the free amine containing compound remaining was calculated from the moles of acid which reacted with the amine and the initial moles of the amine containing compound present.

In some examples, a mixture of compounds with amine functional groups were used and reacted with a carboxylic acid. To determine the final solution composition of carboxylates of the amines, the acid was assumed to have reacted equally with all amine functional groups present. Thus, the moles of carboxylic acid were divided equally by the number of amine containing groups present in the solvent mixture to determine the amount of the ammonium ion carboxylate formed from each amine. Each carboxylate derived from the amine is identified in the final solution composition.

Abbreviations

MDEA—N-methyldiethanolamine

MHEEA—2-((2(2-hydroxyethoxy)ethyl)(methyl)amino) ethanol

NBPT—N-(n-butyl)thiophosphoric triamide

TEA—triethanolamine

UAN—Urea ammonium nitrate (an aqueous urea ammonium nitrate solution)

Amine G2—a mixture of MDEA and MHEEA and other compounds. The formulation used in all examples contained 74% MHEEA, 22% MDEA and 4% other materials (including 0.3% water) which are referenced in examples as other compounds when Amine G2 is used in the example.

HEM—N-hydroxyethylmorpholine or 2-morpholinoethanol

NFM—N-formylmorpholine or morpholine-4-carbaldehyde

NAM—N-acetylmorpholine or 1-morpholinoethanone

YL6—FDC Yellow Number 6 a colorant

BNVP—OrcoBrite® 4 BN Violet Pigment a colorant

LV5BF—Intrabond® Liquid Violet 5BF a colorant.

General Procedures

Viscosity was measured using a Brookfield viscometer (LVDVII). Viscosity was measured at 6° C. temperature intervals from 36° C. to 18° C. (or 12° C.).

Volatile nitrogen losses were measured at 22° C. using equipment described by Woodard et. al. ("Design and Validation of a Laboratory System for Measurement of Volatilized Ammonia" Agronomy Journal Volume 103 Pages 38-44, 2011). Samples were applied to the surface of bare soil with moisture content from 15% to 17% water. The head space was swept at a rate of 1 L/min with moisture saturated air into an acid trap containing 50 mL of 0.04 M $H_2SO_4$. The ammonia collected by the acid was determined by colorimetric method using a flow injection analyzer (Lachat 8500A).

Examples of NBPT Solutions Prepared from Hydroxyethylmorpholine

The following examples represent solutions prepared according to the invention containing NBPT dissolved in the N-substituted morpholine, hydroxyethylmorpholine (HEM), with or without pH adjustment. Additionally, examples are included wherein a solvent mixture composed of N-substituted morpholine, hydroxyethylmorpholine (HEM), and either an alkanolamine or a mixture of an alkyl substituted amino alcohol with an alkoxyalkyl substituted amino alcohol was used to dissolve NBPT in a pH adjusted solvent mixture.

Viscosity, density, pH and freezing point of the solutions from examples 1-7 and example 19 are shown in table 1. To conserve space only the viscosity data for 18° C. is shown.

Example 1

A solution containing 20% NBPT was prepared by dissolving 33.15 g of NBPT into of 130.0 g of hydroxyethylmorpholine (HEM). The solution was formed by heating the mixture until the temperature reached 45° C. and holding the temperature until the NBPT had dissolved. After forming the solution, 1.37 g of glacial acetic acid was added to adjust the pH to 8.06, and then 0.85 g of FDC Yellow Number 6 (YL6) was added. The final solution contained 20.00% NBPT, 76.61% HEM, 2.63% of the acetate of HEM. 0.51% YL6, and 0.25% of water.

Example 2

A solution containing 26% NBPT was prepared by dissolving 46.64 g of NBPT into 130.0 g of HEM. The solution was prepared in the same manner as example 1 using 1.37 g of glacial acetic acid to adjust the pH to 8.21 and coloring the solution with 0.92 g of YL6. The solution contained 26.07% NBPT, 70.75% HEM, 2.44% of the acetate of HEM, 0.51% YL6 and 0.23% water

Example 3

A solution containing 30% NBPT was prepared by dissolving 43.60 g of NBPT into 100.0 g of HEM. The solution was prepared in the same manner as example 1, the pH was adjusted to 8.32 with 0.60 g of glacial acetic acid, and the solution was colored by adding 0.59 g of OrcoBrite® 4 BN violet pigment solution (4BNVP). The final solution contained 30.07% NBPT, 68.08% HEM, 1.32% of the acetate of HEM, 0.41% of OrcoBrite® 4BN (4BNVP), and 0.12% water.

Example 4

A solution containing 36% NBPT was prepared by dissolving 57.30 g of NBPT into 100.0 g of HEM. The solution was prepared as described in example 1, the pH was adjusted with 0.55 g of glacial acetic acid to 8.40 and the solution was colored by adding 0.64 g of 4BNVP. The solution contained 36.12% NBPT, 62.27% HEM, 1.10% of the acetate of HEM, 0.40% 4BNVP, 0.10% water

Example 5

A 24% solution of NBPT in HEM without pH adjustment was prepared by dissolving 31.80 g of NBPT in 100.0 g of HEM as described in example 1. After dissolving the NBPT, 0.54 g of 4BNVP was added to color the solution. The final solution contained 75.56% HEM, 24.03% NBPT and 0.41% 4BNVP and had a pH of 8.65.

Example 6

A 30% solution of NBPT was prepared in a mixture of HEM and an alkanolamine (TEA), by combining 50.0 g of HEM with 50.0 g of TEA and then dissolving 42.40 g of NBPT as described for example 1. After dissolving the NBPT, 1.05 g of glacial acetic acid was added to adjust the pH to 8.66 and then 0.55 g of 4BNVP was added to color the solution. The final solution contained: 34.15% HEM, 34.11% TEA, 30.32% NBPT, 0.41% 4BNVP, 0.08% water and 0.44 and 0.48% of the acetates of HEM and TEA, respectively.

Example 7

A 24% solution of NBPT was prepared in a mixture of HEM and alkylsubstitued amino alcohol (MDEA) and an alkoxy alkyl substituted amino alcohol (MHEEA) by combining 50.00 g of HEM with 50.00 g of Amine G2 (74% MHEEA and 22% MDEA, 4% other materials) and then dissolving 32.20 g of NBPT as described in example 1. After dissolving the NBPT, 1.05 g of acetic acid was added to adjust the pH to 8.56 and 0.55 g of 4BNVP was added to color the solution. The final solution contained: 36.66% HEM. 26.84% MHEEA, 7.67% MDEA, 24.12% NBPT, 0.41% 4BNVP, 0.23% water (0.004% from amine G2), 1.49% other compounds except water and 0.83%, 0.97% and 0.78% of the acetates of HEM, MHEEA and MDEA, respectively.

Example of Solutions Prepared from Amido Substituted Morpholines

The following examples represent solutions prepared according to the invention containing NBPT dissolved in the N-substituted morpholines in which an amido functional group is attached to the nitrogen of morpholine (such as N-formyl morpholine —NFM, or N-acetyl morpholine —NAM). The pH of some NBPT containing solutions of the examples was adjusted with a carboxylic acid. The examples using NFM or NAM may include the addition of a carboxylic acid for pH adjustment. Additionally, examples are included wherein a solvent mixture composed of HEM and either NFM or NAM was used to prepare a pH adjusted NBPT solution. Additional examples include NBPT containing solutions (pH adjusted) were formed by the use of NAM or NFM with an alkanolamine or a mixture of alkyl substituted amino alcohols. One example represents a pH adjusted mixture of HEM, NFM and a mixture of alkyl substituted amino alcohols.

The viscosity, density, pH and freezing point of the solutions from examples 8-18 are shown in table 2. To conserve space only the viscosity data for 18° C. is shown.

Example 8

A 24% solution of NBPT in N-formylmorpholine (NFM) was prepared by adding 22.33 g of NBPT to 70.00 g of NFM and dissolving the NBPT by heating to 45° C. and holding the mixture at 45° C. until all NBPT was dissolved. After dissolving the NBPT 0.47 g of YL6 was added to give an orange color to the solution. The final solution contained: 75.44% NFM, 23.95% NBPT and 0.51% YL6 and had a pH of 8.41.

Example 9

A 26% solution of NBPT in N-formylmorpholine (NFM) was prepared by adding 25.06 g of NBPT to 70.00 g of NFM and dissolving the NBPT by heating to 45° C. and holding the mixture at 45° C. until all NBPT was dissolved. After dissolving the NBPT, 0.74 g of glacial acetic acid was added to adjust the pH to 8.50 and then 0.39 g of 4BNVP to give a purple color to the solution. The final solution contained: 72.77% NFM, 26.05% NBPT, 0.77% acetic acid and 0.41% 4BNVP. The solution formed soap like material after addition of the pigment which did not remain in solution.

Example 10

A 24% solution of NBPT was prepared from a mixture of NFM and HEM by combining 35.00 g of HEM with 35.00 g of NFM and dissolving 22.51 g of NBPT into the combined mixture of solvents. The NPT was dissolved as described in example 9 and then 0.35 g of glacial acetic acid was added to adjust the pH to 8.24. The solution was colored by addition of 0.39 g of 4BNVP. The final solution contained: 37.49% NFM, 36.67% HEM, 24.11% NBPT, 1.19% of the acetate of HEM 0.42% 4BNVP and 0.11% water.

Example 11 a 24% solution of NBPT in N-acetylmorpholine (NAM) was prepared by dissolving 22.33 g of NBPT in 70.00 g of NAM as described for example 9. After dissolving the NBPT 0.47 g of YL6 was added to give the solution an orange color. The final solution contained: 75.44% NAM, 23.95% NBPT and 0.51% YL6 and had a pH of 8.58.

Example 12

A pH adjusted 26% solution of NBPT in NAM was prepared by adding 25.06 g of NBPT to 70.00 g of NAM and dissolving the NBPT by heating to 45° C. and holding the mixture at 45° C. until all NBPT was dissolved. After dissolving the NBPT, 1.10 g of glacial acetic acid was added to adjust the pH to 8.43 and then 0.39 g of 4BNVP to give a purple color to the solution. The final solution contained: 72.50% NFM, 25.96% NBPT, 1.14% acetic acid and 0.40% 4BNVP. The solution formed soap like material after addition of the pigment which did not remain in solution.

Example 13

A pH adjusted 24% solution of NBPT dissolved in a mixture of HEM and NAM was prepared by combining 35.00 g of HEM and 35.00 g of NAM and dissolving the NBPT as described in example 12. After dissolving the NBPT, 0.74 g of glacial acetic acid was added to adjust the pH to 8.23 and then 0.80 g of a solution of a purple dye was added to give the solution a purple color. The final solution contained: 37.13% NAM, 35.41% HEM, 23.88% NBPT, 2.50% of the acetate of HEM, 0.84% of purple dye, and 0.24% water.

Example 14

A pH adjusted 24% solution of NBPT dissolved in a mixture of TEA and NFM was prepared by mixing 35.00 g of TEA and 35.00 g of NFM and dissolving 22.40 g of NBPT into the mixture as described for examples 12. After dissolving the NBPT 0.15 g of glacial acetic acid was added to adjust the pH to 8.72 and then 0.39 of 4BN purple pigment was added to color the solution. The final solution contained: 37.64% NFM, 37.24% TEA, 24.09% NBPT, 0.56% of the acetate of TEA, 0.43% of 4BN pigment and 0.04% water.

Example 15

A pH adjusted 24% solution of NBPT dissolved in a mixture of NFM and amine G2 was prepared by mixing 35.00 g of amine G2 with 35.00 g of NFM and then dissolving 22.51 g of NBPT as described in example 12. After dissolving the NBPT, 0.65 g of glacial acetic acid was added to adjust the pH to 8.82 and then 0.39 g of 4BN violet pigment was added to color the solution. The final solution contained: 37.34% NFM, 26.69% MHEEA, 24.01% NBPT, 7.53% MDEA, 1.29% of the acetate of MHEEA, 1.03% of the acetate of MDEA, 0.42% 4BN violet pigment, 0.21% water (0.004% from Amine G2) and 1.48% other compounds.

Example 16

A pH adjusted 24% solution of NBPT dissolved in a mixture of TEA and NAM was prepared by mixing 35.00 g of TEA and 35.00 g of NAM and dissolving 22.40 g of NBPT into the mixture as described for example 12. After dissolving the NBPT 0.42 g of glacial acetic acid was added to adjust the pH to 8.50 and then 0.81 g of LV5BF dye was added to color the solution. The final solution contained: 37.33% NAM, 36.22% TEA, 28.89% NBPT, 1.56% of the acetate of TEA, 0.81% of LV5BF pigment and 0.14% water.

Example 17

A pH adjusted 24% solution of NBPT dissolved in a mixture of NAM and Amine G2 was prepared by mixing 35.00 g of Amine G2 with 35.00 g of NFM and then dissolving 22.51 g of NBPT as described in example 12. After dissolving the NBPT, 0.55 g of glacial acetic acid was added to adjust the pH to 8.89 and then 0.80 g of 4BN violet pigment was added to color the solution. The final solution contained: 37.39% NAM, 26.87% MHEEA, 24.05% NBPT, 7.64% MDEA, 1.09% of the acetate of MHEEA, 0.88% of the acetate of MDEA, 0.42% LV5BF, 0.18% water (0.004% from Amine G2) and 1.48% other compounds.

Example 18

A pH adjusted 24% solution of NBPT in a mixture of HEM, NFM and Amine G2 prepared by mixing 34.00 g of amine G2 with 33.00 g of NFM and 33.00 g of HEM and then dissolving 31.96 g of NBPT as described in example 12. After dissolving the NBPT, the pH was adjusted by addition of 0.30 g of glacial acetic acid and then 0.51 g of YL6 was added to color the solution. The final solution contained: 24.82% NFM, 24.60% HEM, 18.66% MHEEA, 5.43% MDEA, 24.03% NBPT, 0.31 of the acetate of HEM, 0.36% of the acetate of MHEEA, 0.29% of the acetate of MDEA, 0.38% YL6, 0.10% water (0.003% from Amine G2) and 1.02% other compounds. The pH of the final solution was 9.07.

Additional Solution Examples

Example 19

A pH adjusted solution of NBPT dissolved in HEM was prepared by dissolving 32.50 g of NBPT into 100.00 g of HEM as described in example 1, adjusting the pH to 8.06 with 1.05 g of glacial acetic acid and then adding 0.36 g of 4BNVP colorant. The final solution contained: 73.03% HEM, 23.97% NBPT, 2.50% of the acetate of HEM, 0.26% 4BNVP, and 0.24% water.

Examples of Coated Urea Granules Containing NBPT

In the following examples, NBPT coated urea granules were prepared by adding a pH adjusted solution of NBPT dissolved in an a N-substituted morpholine (NSM) such as HEM, NFM or NAM, a mixture of a N-substituted morpholine such as HEM with an alkanolamine (TEA), or mixture of an N-substituted morpholine with alkyl substituted amino alcohol (MDEA) and an alkoxy alkyl substituted amino alcohol (MHEEA) to granular urea and then mixing to distribute the liquid over the granular urea surface.

Volatile nitrogen losses were measured for products produced in examples 20, 21, 22, 24, 25, and 28 are shown in table 3. To conserve space only the nitrogen losses at 3 days, 7 days and 14 days are shown.

Example 20

A coated urea granular product was prepared from the pH adjusted NBPT containing solution prepared with HEM of example 3. The NBPT treated urea was prepared by adding 1.7 g of the liquid NBPT containing solution of Example 3 to 500.0 g of granular urea then mixing the combined materials until the NBPT solution was visually distributed throughout the granular material. The final product would have a fertilizer analysis of 45.8-0-0. The product would contain 99.66% urea, 0.23% HEM, 0.10% NBPT, 0.01% 4BNVP, 0.005% of the acetate of HEM, 0.00041% water.

Example 21

A coated urea granular product was prepared from NBPT containing solution prepared with HEM of example 5. The NBPT treated product was formed by adding 1.7 g of the liquid NBPT containing solution of Example 5 to 500.0 g of granular urea, mixing the combined materials until the NBPT solution was visually distributed throughout the granular material. The final product would have a fertilizer analysis of 45.8-0-0. The product would contain 99.66% urea, 0.26% HEM, 0.08% NBPT, 0.001% 4BNVP, 0.005% of the acetate of HEM, 0.00041% water.

Example 22

A coated urea granular product was prepared from the pH adjusted NBPT containing solution prepared with HEM and TEA of example 6. The NBPT treated product was formed by adding 1.7 g of the liquid NBPT containing solution of Example 6 to 500.0 g of granular urea then mixing the combined materials until the solution was visually distributed throughout the granular material. The final product would have a fertilizer analysis of 45.8-0-0. The product would contain 99.66% urea, 0.12% HEM, 0.12% TEA, 0.10% NBPT, 0.001% 4BNVP, 0.0001% of the acetate of HEM, 0.002% of the acetate of TEA and 0.0003% water.

Example 23

A coated urea granular product was prepared from the pH adjusted NBPT containing solution prepared with HEM and Amine G2 of example 7. The NBPT treated product was formed by adding 1.7 g of the liquid NBPT containing solution of Example 7 to 500.0 g of granular urea then mixing the combined materials until the solution was visually distributed throughout the granular material. The final product would have a fertilizer analysis of 45.8-0-0. The product would contain 99.66% urea, 0.12% HEM, 0.08% NBPT, 0.09% MHEEA, 0.03% MDEA, 0.01%, 0.01% of the acetates of HEM, MHEEA, and MDEA (0.003% acetate of HEM, 0.004% acetate of MHEEA, 0.003% acetate of MDEA), 0.001% 4BNVP, 0.005% other compounds except water and 0.0008% water.

Example 24

A coated urea granular product was prepared from NBPT containing solution prepared with NFM of example 8. The NBPT treated product was formed by adding 1.7 g of the liquid NBPT containing solution of Example 8 d to 500.0 g of granular urea then mixing the combined materials until the solution was visually distributed throughout the granular material. The final product would have a fertilizer analysis of 45.8-0-0. The product would contain 99.66% urea, 0.26% NFM, 0.08% NBPT, and 0.002% YL6.

Example 25

A coated urea granular product was prepared from NBPT containing solution prepared with NAM of example 11. The NBPT treated product was formed by adding 1.7 g of the liquid NBPT containing solution of Example 11 to 500.0 g of granular urea then mixing the combined materials until the solution was visually distributed throughout the granular material. The final product would have a fertilizer analysis of 45.8-0-0. The product would contain 99.66% urea, 0.26% NAM, 0.08% NBPT, and 0.002% YL6.

Example 26

A coated granular urea product was made using the pH adjusted solution if NBPT in a mixture of HEM and NAM of example 13. The NBPT treated product was formed by adding 1.7 g of NBPT containing liquid of example 13 to 500.0 g of urea then mixing the combined mass mixed to distribute the liquid throughout the granular product. The final product would have a fertilizer analysis of 45.8-0-0. The final product contained: 99.6% urea, 0.13% HAM, 0.12% HEM, 0.08% NBPT, 0.01% of the acetate of HEM, 0.003% of 5BFLV, and 0.0008% water.

Example 27

A NBPT coated granular urea product was prepared suing granular urea, the pH adjusted NBPT solution prepared with NFM and Amine G2 of example 15. The NBPT treated product was formed by adding 1.7 g of NBPT containing liquid of example 15 to 500.0 of granular urea the mixing the combined materials to distribute the liquid throughout the granular material. The final product had a fertilizer analysis of 45.8-0-0 contained: 99.66% urea, 0.13% NFM, 0.09% MHEEA, 0.08% NBPT, 0.03% of MDEA. The remaining 0.01% of the product was composed of 0.004% of the acetate of MHEEA, 0.003% of the acetate of MDEA, 0.001% of 4BNVP, 0.0007% water and 0.003% other compounds.

Example 28

A coated urea granular product was prepared from the pH adjusted NBPT containing solution prepared with HEM of example 19. The NBPT treated urea was prepared by adding 1.7 g of the liquid NBPT containing solution of Example 19 to 500.0 g of granular urea then mixing the combined materials until the NBPT solution was visually distributed throughout the granular material. The final product would have a fertilizer analysis of 45.8-0-0. The product would contain 99.66% urea, 0.25% HEM, 0.08% NBPT, 0.0008% 4BNVP, 0.008% of the acetate of HEM, and 0.0008%.

Preparation of Coated Granular Fertilizers Containing NBPT and Additional Nutrients In the following examples, NBPT containing coated granular urea fertilizers are prepared by addition of a solution of NBPT dissolved in a solution of the present invention described above and adding additional nutrients in a powdered form of a commercially available plant nutrient supplying substance. The procedure generally followed in the examples involves first forming and NBPT treated urea granule by adding the NBPT containing liquid to the urea, mixing to distribute the NBPT containing liquid, adding the powder and with continuous mixing adding any additional binding liquid required. The additional binding liquid is identified below and within the text of the examples when where the liquid was used. In several examples, the NBPT treated urea was stored overnight (approximately 12 hours) before proceeding with the remainder of the process to form the NBPT containing granule with additional plant nutrients.

Example 29

A phosphate coated granular urea fertilizer with an analysis of 39-9-0 with 0.14% B containing 0.10% NBPT was prepared using the pH adjusted NBPT containing solution of example 19 with NBPT dissolved in HEM, urea, and monoammonium phosphate powder (MAP powder). The additional binding liquid required was provided by Arborite® Binder 77 (triethanolamine borate 6% B—Encee Chemical Sales, North Carolina, USA). To prepare the product material; 500.00 g of urea was treated with 2.50 g of the NBPT solution of example 5 forming an NBPT treated granular urea. To the NBPT treated urea, 107.30 g of MAP powder was added and mixing was initiated and while mixing 13.00 g of Arborite® Binder 77 was added to cause the powdered MAP to adhere to the NBPT treated urea. The final product contained: 80.29% urea, 17.23% monoammonium phosphate, 2.08% of the boron containing mixture (Arborite® Binder 77), and 0.40% of the NBPT containing solution of example 19. Within the final product the NBPT solution of example 19 contributed the following materials: 0.29% HEM, 0.10% NBPT, 0.01% of the acetate of HEM, 0.001% water, and 0.0001% 4BNVP. The projected fertilizer analysis was 39.00% N, 8.96% $P_2O_5$ with 0.13% boron and 0.10% NBPT.

Example 30

A phosphate coated granular urea fertilizer with an analysis of 39-9-0 with 0.14% B containing 0.10% NBPT was prepared using the pH adjusted NBPT containing solution of example 19 with NBPT dissolved in NFM, urea, and monoammonium phosphate powder (MAP powder). The additional binding liquid required was provided by Arborite® Binder 77 (triethanolamine borate 6% B—Encee Chemical Sales, North Carolina, USA). To prepare the product material; 500.00 g of urea was treated with 2.50 g of the NBPT solution of example 8 forming an NBPT treated granular urea. 107.30 g of MAP powder was added and mixing was initiated and while mixing 13.00 g of Arborite® Binder 77 was added to cause the powdered MAP to adhere to the NBPT treated urea. The final product contained: 80.29% urea, 17.23% monoammonium phosphate, 2.08% of the boron containing mixture (Arborite® Binder 77), and 0.40% of the NBPT containing solution of example 8. Within the final product the NBPT solution of example 8 contributed the following materials: 0.30% NFM, 0.10% NBPT, 0.01% of the acetate of HEM, and 0.0002% YL6. The projected fertilizer analysis was 39.00% N, 8.96% $P_2O_5$ with 0.13% boron and 0.10% NBPT.

To prepare several examples below a triethanolamine acetate solution was used as the source of additional liquid for the preparation of the nutrient coated urea products. The triethanolamine acetate solution used was prepared by adding 59.80 g of glacial acetic acid to 400.00 g of triethanolamine. The final pH of the mixture was 7.21 and the solution contained: 43.62% triethanolamine acetate, 52.63% triethanolamine, and 3.75% $H_2O$.

Example 31

A nitrogen, potassium and sulfur supplying fertilizer was prepared from urea, powdered potassium sulfate, a triethanolamine acetate solution, and the pH adjusted NBPT containing solution of example 19 prepared with HEM. The product was produced by: 1) forming an NBPT treated urea by adding 2.11 g of NBPT solution of example 19 (pH adjusted HEM) to 500.00 g of granular urea and mixing to distribute the NBPT solution, 2) adding 113.10 g of potassium sulfate powder and initiating mixing, and 3) adding 12.40 g of triethanolamine acetate solution while mixing to cause the powdered potassium sulfate to adhere to the NBPT treated urea of step 1. The final product contained: 79.67% urea, 18.02% potassium sulfate, 1.97% triethanolamine acetate and 0.33% of the pH adjusted NBPT solution of example 19. The materials contributed to the final product by the NBPT containing solution of example 19 were: 0.25% HEM, 0.08% NBPT, 0.01% of the acetate of HEM, 0.0004% 4BNVP, and 0.0008% water. The fertilizer analysis of the product was 36.65% N, 9.01% $K_2O$, 3.24% 5 and 0.08% NBPT.

Example 32

Another nitrogen, potassium an sulfur supplying fertilizer was prepared from urea, powdered potassium sulfate, a triethanolamine acetate solution, and the pH adjusted NBPT containing solution of example 19 prepared with HEM. The procedure of example 31 was followed except that the NBPT treated urea was stored overnight and 13.35 g of triethanolamine acetate solution was used. The final product contained: 79.55% urea, 17.99% potassium sulfate, 2.12% triethanolamine acetate and 0.34% of the pH adjusted NBPT solution of example 19. The materials contributed to the final product by the NBPT containing solution of example 19 were: 0.25% HEM, 0.08% NBPT, 0.01% of the acetate of HEM, 0.0008% 4BNVP, and 0.0008% water. The fertilizer analysis of the product was 36.59% N, 9.00% $K_2O$, 3.23% S and 0.08% NBPT.

To prepare several examples below a saturated ammonium sulfate solution was used to supply the additional binding liquid needed. To form the saturated ammonium sulfate solution 44.44 g of $(NH_4)_2SO_4$ was dissolved in 55.56 g of water. The solution contained a small layer of crystals of ammonium sulfate indicating the it was saturated in ammonium sulfate.

Example 33

A volatility inhibited nitrogen, potassium, calcium and sulfur supplying fertilizer was prepared from urea, powdered potassium sulfate, powdered gypsum, a, and the pH adjusted NBPT containing solution of example 19 prepared with HEM in a multiple step coating process. The additional binding liquid was provided by a saturated ammonium sulfate solution (see above). The product was formed in three steps: 1) An NBPT treated urea was formed by adding 1.90 g of the NBPT containing solution of example 19 to 400.00 g of urea and mixing the materials to distribute the NBPT containing liquid, 2) adding 91.20 g of powdered potassium sulfate and 64.00 g of powdered gypsum to the NBPT treated urea and initiating mixing, 3) adding 12.40 g of saturated ammonium sulfate solution while continuing to mix to cause the powders to adhere to the NBPT treated urea. The final product contained: 70.24% urea, 16.01% potassium sulfate, 11.24% gypsum, 2.18% saturated ammonium sulfate, and 0.33% of the NBPT containing solution of example 19. The NBPT containing solution contributed the following to the final product: 0.24% HEM, 0.08% NBPT, 0.01% of the acetate of HEM, 0.0009% of 4BNVP colorant, and 0.0008% water. The fertilizer analysis was: 32.51% N, 8.01% $K_2O$, 3.11% S, 2.02% Ca and 0.08% NBPT.

Example 34

A volatility inhibited nitrogen calcium and sulfur supplying fertilizer was prepared from urea, gypsum powder, the NBPT containing solution of example 8 prepared with NFM and the triethanolamine acetate solution described above. The granular product was formed by: 1) forming an NBPT treated urea by adding 1.98 g of NBPT containing solution from example 8 to 500.00 g of granular urea and mixing to distribute the liquid, 2) adding 81.00 g of powdered gypsum to the NBPT treated urea and initiating mixing, and 3) adding 4.15 g of triethanolamine acetate solution while continuing to mix to cause the powder to adhere to the NBPT treated urea. The final granular product contained: 85.16% urea, 13.80% gypsum, 0.70% triethanolamine acetate, and 0.33% of the NBPT containing solution of example 8. The NBPT containing solution of example 8 contributed the following to the final product: 0.25% NFM, 0.08% NBPT, 0.01% and 0.002% 4BNVP. The fertilizer analysis of the product was: 39.20% N, 2.48% calcium, 3.04% sulfur and 0.08% NBPT.

Example 35

A volatility inhibited nitrogen calcium and sulfur supplying fertilizer was prepared from urea, gypsum powder, the NBPT containing solution of example 8 prepared with HEM and a triethanolamine acetate solution described above. The product was formed in the same manner as example 34 except that the NBPT treated urea was stored overnight and 8.40 g of triethanolamine acetate was used to cause the powder to adhere to the urea. The final granular product contained: 84.55% urea, 13.70% gypsum, 1.42% triethanolamine acetate, and 0.33% of the NBPT containing solution of example 19. The NBPT containing solution of example 19 contributed the following to the final product: 0.25% HEM, 0.08% NBPT, and 0.002% 4BNVP. The fertilizer analysis of the product was: 38.94% N, 2.47% calcium, 3.01% sulfur and 0.08% NBPT.

Example 36

A volatility inhibited granular fertilizer supplying nitrogen, zinc, and sulfur was prepared using granular urea, zinc sulfate powder (35% Zn), the triethanolamine acetate solution described above, zinc stearate, and the pH adjusted NBPT containing solution of example 19. The granular product was formed by: 1) forming an NBPT treated urea by adding 1.68 g of the NBPT containing solution of example 19 to 400.00 g of urea and mixing to distribute the liquid, 2) adding 85.07 g of zinc sulfate powder (35% Zn) and initiating mixing, 3) adding 16.61 g of triethanolamine acetate while mixing to cause the zinc sulfate powder to adhere, and 4) adding 3.22 g of zinc stearate powder and continuing to mix the combined ingredients until the zinc stearate adhered. The zinc stearate was added to break a pile set which often forms in zinc coated urea. The final product contained: 78.96% urea, 16.79% zinc sulfate, 3.28% triethanolamine acetate, 0.64% zinc stearate, and 0.33% of the pH adjusted NBPT containing solution of example 19. The NBPT containing solution contributed the following to the final product: 0.24% HEM, 0.08% NBPT, 0.01% of the acetate of HEM, 0.0008% water, and 0.0009% 4BNVP colorant.

Example 37

A volatility inhibited nitrogen, zinc and sulfur supplying fertilizer was prepared from urea, zinc sulfate powder (35% Zn), the NBPT containing solution of example 19 prepared with HEM and a triethanolamine acetate solution described above. The product was prepared as in example 36 except that the NBPT treated urea was stored over night, and only 13.02 g of triethanolamine acetate solution was used. The final product contained: 79.53% urea, 16.91% zinc sulfate, 2.59% triethanolamine acetate, 0.64% zinc stearate, and 0.33% of the pH adjusted NBPT containing solution of example 19. The NBPT containing solution contributed the following to the final product: 0.24% HEM, 0.08% NBPT, 0.01% of the acetate of HEM, 0.0008% water, and 0.0009% 4BNVP colorant.

Example 38

A volatility inhibited fertilizer supplying nitrogen, zinc, calcium, and sulfur was prepared from granular urea, zinc sulfate powder (35% Zn), gypsum powder, zinc stearate, the triethanolamine acetate solution (described above) and the pH adjusted NNBPT containing solution of example 10 (NFM and HEM). The granular product was formed by: 1) forming an NBPT treated granular urea by adding 1.79 g of the NBPT containing solution of example 10 to 400.00 g of urea and mixing to distribute the liquid, 2) allowing the NBPT treated urea to stand overnight, 3) adding 85.07 g of powdered zinc sulfate to the NBPT treated urea and initiating mixing and then adding 12.9 g of triethanolamine acetate solution and continuing mixing to cause the powdered zinc sulfate to adhere to the NBPT treated urea, 4) adding 12.80 g of powdered gypsum while mixing, and 5) adding 3.22 g of powdered zinc stearate while mixing to prevent a pile set upon storage. The final product contained: 77.56% urea, 16.49% zinc sulfate, 2.48% gypsum, 2.50% triethanolamine acetate, 0.62% zinc stearate and 0.34% of the NBPT pH adjusted containing solution of example 10. The NBPT solution of example 10 contributed the following to the final product: 0.13% NFM, 0.13% HEM, 0.08% NBPT, 0.004% of the acetate of HEM, 0.001% 4BNVP colorant, and 0.0004% water. The fertilizer analysis of the final product was 35.87% N, 5.9% Zn, 2.96% S, 0.06% Ca, and 0.08% NBPT.

Examples of Treating UAN Solutions

Urea ammonium nitrate is a commonly used liquid fertilizer solution containing from 26% N to 32% N. For the examples described below a 32% N solution was used which contains 32.5% urea, 44.5% $NH_4NO_3$, and 23% $H_2O$ and has density of 1.33 g/mL.

Example 39

The NBPT containing solution of example 5 was used to treat UAN solution by adding 0.433 g of the solution of example 5 to 400.00 g of UAN solution. The NBPT containing solution distributed throughout the UAN solution with very little agitation. The final treated UAN solution contained 0.080% NBPT on the basis of the urea present or 0.021% NBPT on a total weight of UAN solution. The final product contained on a total weight basis 0.065% HEM and 0.0004% of 4BNVP colorant.

Example 40

The formation of treated UAN solution of example was repeated using the NBPT solution dissolved in NFM of example 8. The procedure followed was the same as example 39. The final treated UAN solution contained 0.080% NBPT on the basis of the urea present or 0.021% NBPT on a total weight of UAN solution. The final product contained on a total weight basis 0.065% NFM and 0.0004% of YL6 colorant.

Example 42

The formation of treated UAN solution of example was repeated using the NBPT solution dissolved in NAM of example 11. The procedure followed was the same as example 39. The final treated UAN solution contained 0.080% NBPT on the basis of the urea present or 0.021% NBPT on a total weight of UAN solution. The final product contained on a total weight basis 0.065% NAM and 0.0004% of YL6 colorant.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A solution for use in reducing nitrogen volatilization comprising N-(n-butyl)-thiophosphoric triamide (NBPT) dissolved in one or more N-substituted morpholines having a morpholine heterocyclic ring with an N-atom to which a carbon chain including an oxygen atom is attached.

2. The solution of claim 1, wherein said N-substituted morpholines have the formula:

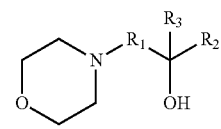

where $R_1$ is a carbon chain from 1 to 4 carbon atoms and $R_2$ and $R_3$ are either hydrogen or carbon chains with from 1 to 4 carbons.

3. The solution of claim 1, wherein said N-substituted morpholines have the formula:

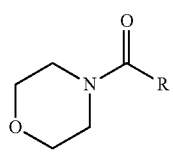

where R is either a hydrogen or a carbon chain with 1 to 4 carbon atoms.

4. The solution of claim 2, wherein said N-substituted morpholine is N-hydroxyethylmorpholine (HEM) (2-morpholinoethanol), morpholinomethanol, 1-morpholinopropan-2-ol, 1-morpholinobutan-2-ol, 2-methyl-1-morpholinopropan-2-ol, 4-morpholinobutan-2-ol, 3-morpholinopropan-1-ol, and 1-morpholinopropan-1-ol or mixtures thereof.

5. The solution of claim 3, wherein said N-substituted morpholine is N-formylmorpholine (NFM), N-acetylmorpholine (NAM), 1-morpholinopropan-1-one, 2-methyl-1-morpholinopropan-1-one, N-morpholinobutan-1-one, N-lactyl(2-hydroxy-1-morpholinopropane-1-one), 2-hydroxy-1-morpholinoethanone, 3-hydroxy-1-morpholinopropan-1-one, 2-hydroxy-1-morpholinopropan-1-one, 4-hydroxy-1-morpholinobutan-1-one, 3-hydroxy-1-morpholinobutan-1-one, 2-hydroxy-1-morpholinobutan-1-one, or mixtures thereof.

6. The solution of claim 1, wherein said solution includes from about 0.5% NBPT to about 40% NBPT.

7. The solution of claim 1, wherein said solution is pH adjusted to a pH of from 7 to 10.

8. The solution of claim 1, further including a co-solvent.

9. The solution of claim 1, further including a denitrification inhibitor.

10. The solution of claim 9, wherein said denitrification inhibitor is selected from the group consisting of dicyandiamide (DCD or 2-cyanoguanidine), DMPP (3,4-dimethylpyrazole phosphate), and nitrapyrin (2-chloro-6-(trichloromethyl)pyridine).

11. The solution of claim 1, wherein said NBPT is dissolved in hydroxyethyl morpholine, N-formyl morpholine, N-acetylmorpholine or mixtures thereof.

12. A solution of claim 7 in which the pH is adjusted from 7 to 10.

13. A method of reducing the nitrogen volatility of a urea fertilizer comprising combining said fertilizer with N-(n-butyl)-thiophosphoric triamide (NBPT) dissolved in N-hydroxyethyl morpholine, N-formyl morpholine, N-acetylmorpholine or mixtures thereof.

14. The method of claim 13, wherein said urea fertilizer is in aqueous solution.

15. The method of claim 13, wherein said urea fertilizer is granular and said solution is coated onto said granules.

16. The method of claim 13, wherein said NBPT comprises from about 0.005% to about 0.25% by weight of the combined urea fertilizer and solution.

17. The method of claim 13, wherein said solution includes from about 0.5% NBPT to about 40% NBPT.

18. The method of claim 13, wherein said solution is pH adjusted to a pH of from 7 to 10.

19. The method of claim 13, further including adding a co-solvent.

20. The method of claim 13, further including adding a denitrification inhibitor.

21. The method of claim 20, wherein said denitrification inhibitor is selected from the group consisting of dicyandiamide (DCD or 2-cyanoguanidine), DMPP (3,4-dimethylpyrazole phosphate), and nitrapyrin (2-chloro-6-(trichloromethyl)pyridine).

22. The method of claim 13, further including adding additional plant nutrients.

23. The method of claim 13, wherein said solution is less than 5% of said fertilizer.

24. The method of claim 13, further including adding an aqueous diluent.

25. A urea fertilizer having reduced nitrogen volatility comprised of urea and N-(n-butyl)-thiophosphoric triamide (NBPT) dissolved in one or more N-substituted morpholines having a morpholine heterocyclic ring with an N-atom to which a carbon chain including an oxygen atom is attached.

26. The urea fertilizer of claim 25, wherein said N-substituted morpholines have the formula:

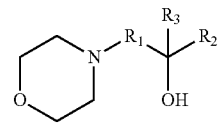

where $R_1$ is a carbon chain from 1 to 4 carbon atoms and $R_2$ and $R_3$ are either hydrogen or carbon chains with from 1 to 4 carbons.

27. The urea fertilizer of claim 25, wherein said N-substituted morpholines have the formula:

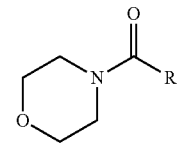

where R is either a hydrogen or a carbon chain with 1 to 4 carbon atoms.

28. The urea fertilizer of claim 26, wherein said N-substituted morpholine is N-hydroxyethyl morpholine (HEM) (2-morpholinoethanol), morpholinomethanol, 1-morpholinopropan-2-ol, 1-morpholinobutan-2-ol, 2-methyl-1-morpholinopropan-2-ol, 4-morpholinobutan-2-ol, 3-morpholinopropan-1-ol, and 1-morpholinopropan-1-ol or mixtures thereof.

29. The urea fertilizer of claim 27, wherein said N-substituted morpholine is N-formylmorpholine (NFM), N-acetylmorpholine (NAM), 1-morpholinopropan-1-one, 2-methyl-1-morpholinopropan-1-one, N-morpholinobutan-1-one, N-lactyl(2-hydroxy-1-morpholinopropane-1-one), 2-hydroxy-1-morpholinoethanone, 3-hydroxy-1-morpholinopropan-1-one, 2-hydroxy-1-morpholinopropan-1-one, 4-hydroxy-1-morpholinobutan-1-one, 3-hydroxy-1-morpholinobutan-1-one, 2-hydroxy-1-morpholinobutan-1-one, or mixtures thereof.

30. The urea fertilizer of claim 25, wherein said fertilizer includes from about 0.5% NBPT to about 40% NBPT.

31. The urea fertilizer of claim 25, wherein said fertilizer is pH adjusted to a pH of from 7 to 10.

32. The urea fertilizer of claim 25, further including a co-solvent.

33. The urea fertilizer of claim 25, further including a denitrification inhibitor.

34. The urea fertilizer of claim 33, wherein said denitrification inhibitor is selected from the group consisting of dicyandiamide (DCD or 2-cyanoguanidine), DMPP (3,4-dimethylpyrazole phosphate), and nitrapyrin (2-chloro-6-(trichloromethyl)pyridine).

35. The urea fertilizer of claim 25 in aqueous solution.

36. The urea fertilizer of claim 25, wherein said urea is granular urea, said granular urea being coated with N-(n-butyl)-thiophosphoric triamide (NBPT) dissolved in one or more N-substituted morpholines and mixtures thereof.

37. The urea fertilizer of claim 25, further including additional plant nutrients.

* * * * *